United States Patent [19]
Bodor

[11] Patent Number: 5,981,517
[45] Date of Patent: Nov. 9, 1999

[54] ANDROSTENE DERIVATIVES

[75] Inventor: Nicholas S. Bodor, Gainesville, Fla.

[73] Assignee: Soft Drugs, Inc., Gainesville, Fla.

[21] Appl. No.: 08/840,038

[22] Filed: Apr. 24, 1997

Related U.S. Application Data

[60] Provisional application No. 60/017,102, May 9, 1996.
[51] Int. Cl.⁶ ............................................. A61K 31/56
[52] U.S. Cl. ..................... 514/181; 514/177; 514/178; 552/528; 552/614; 552/616; 552/632
[58] Field of Search .................... 514/177, 178, 514/181; 552/528, 614, 616, 632

[56] References Cited

U.S. PATENT DOCUMENTS

| | | | |
|---|---|---|---|
| 3,258,473 | 6/1966 | Kincl | 260/397.4 |
| 3,636,010 | 1/1972 | Anner et al. | 260/397.1 |
| 3,828,080 | 8/1974 | Phillipps et al. | 260/397.1 |
| 3,856,828 | 12/1974 | Phillipps et al. | 260/397.1 |
| 4,093,721 | 6/1978 | Phillipps et al. | 424/243 |
| 4,188,385 | 2/1980 | Edwards | 424/241 |
| 4,198,403 | 4/1980 | Alvarez | 424/241 |
| 4,263,289 | 4/1981 | Edwards | 424/238 |
| 4,285,937 | 8/1981 | Kalvoda | 424/243 |
| 4,335,121 | 6/1982 | Phillipps et al. | 424/241 |
| 4,607,028 | 8/1986 | Schmidlin | 514/180 |
| 4,650,610 | 3/1987 | Phillipps et al. | 260/397.1 |
| 4,710,495 | 12/1987 | Bodor | 514/174 |
| 4,996,335 | 2/1991 | Bodor | 552/610 |
| 5,021,408 | 6/1991 | Aubard et al. | 514/179 |
| 5,026,693 | 6/1991 | Villax et al. | 514/180 |
| 5,223,493 | 6/1993 | Boltralik | 514/180 |
| 5,362,721 | 11/1994 | Stache et al. | 514/179 |

FOREIGN PATENT DOCUMENTS

| | | |
|---|---|---|
| 0135476 | 3/1985 | Germany . |
| 1384372 | 2/1975 | United Kingdom . |
| 2014579 | 8/1979 | United Kingdom . |
| 1578243 | 11/1980 | United Kingdom . |

OTHER PUBLICATIONS

*Chemical Abstracts*, vol. 105, No. 17, abstract No. 153397 (abstract of JP 61 007291), 1986.

*Patent Abstracts of Japan*, vol. 010, No. 148, C–35 (abstract of JP 61 007291), 1986.

*Database WPI*, Section CH, Week 8608, Derwent Publications Ltd., AN 86–052889 (abstract of JP 61 007291), 1986.

Ueno et al, *J. Med. Chem.*, vol. 34, No. 8, pp. 2468–2473 (1991).

*Primary Examiner*—Dwayne C. Jones
*Attorney, Agent, or Firm*—Burns, Doane, Swecker, & Mathis, L.L.P.

[57] ABSTRACT

The invention provides new androstene derivatives having anti-inflammatory activity, pharmaceutical compositions containing them, and methods of administering them to warm-blooded animals in the treatment of inflammation. The active compounds are alkyl 17α-dichloroacetoxy-11β-hydroxyandrosta-1,4-dien-3-one-17β-carboxylates and related androstenes.

69 Claims, No Drawings

ANDROSTENE DERIVATIVES

CROSS-REFERENCE TO RELATED APPLICATION

This application claims the priority of United States Provisional Patent Application No. 60/017,102, filed May 9, 1996.

TECHNICAL FIELD OF THE INVENTION

The invention relates to new androstene derivatives having anti-inflammatory activity, pharmaceutical compositions comprising said derivatives, new chemical intermediates useful in the preparation of these derivatives, and methods of administering these derivatives to mammals in the treatment of inflammation.

BACKGROUND ART

Topical or other local application of potent glucocorticoids can produce severe toxic effects such as Cushingoid features, pituitary-adrenal suppression, skin atrophy, immunosuppression and inhibition of wound healing. Other kinds of toxic responses, including allergies and cataracts, have resulted from long term use of drugs of this type.

Ophthalmic application of glucocorticosteroids presents additional problems. The protective mechanisms built into the eye allow only small amounts of doses applied to the eye to reach the target sites within the eye; generally, over 90 per cent of the total dose will find its way into the general circulation. This in turn leads to serious systemic side effects of the type described above. Moreover, there is a more serious and specific side effect when these drugs are used in the eye, which is an increase in intraocular pressure (IOP). Corticosteroid-induced chronic or acute glaucoma has in fact been reported since the early 1960's. Generally, the corticosteroid is needed only topically to control the inflammation. However, the absorbed steroid is responsible for the serious side effects noted above. It is believed that the effect of the corticosteroid on the aqueous outflow pathway and adjacent tissue glycosaminoglycans (GAG's) is important in the development of glucocorticoid-induced ocular hypertension.

There is therefore a serious need for potent local anti-inflammatory steroids which lack systemic activity and consequently do not produce the serious systemic side effects associated with drugs of this class.

The natural glucocorticosteroids and many of their marketed derivatives are $\Delta^4$ and $\Delta^{1,4}$ pregnenes having 21-hydroxy substituents. There are, however, a number of anti-inflammatory $\Delta^4$ and $\Delta^{1,4}$ androstenes described in the literature. Thus, Anner et al, U.S. Pat. No. 3,636,010, patented Jan. 18, 1972, describes esters of $\Delta^4$ and $\Delta^{1,4}$-16α-methyl-6α,9α-difluoro-11β,17α-dihydroxy-3-oxo-androstadiene-17-carboxylic acid having "good anti-inflammatory and thymolytic activity." Thymolytic activity is, however, an indication of systemic activity.

In the 1970's and early 1980's several patents have issued describing androstene derivatives which have been purported to have more desirable ratios of anti-inflammatory activity to undesirable side effects. These include British Patent Specification No. 1,384,372; Phillipps et al U.S. Pat. No. 3,828,080; Phillipps et al U.S. Pat. No. 3,856,828; Phillipps et al U.S. Pat. No. 4,093,721; UK Patent Application GB 2,014,579; Edwards U.S. Pat. No. 4,188,385; Alvarez U.S. Pat. No. 4,198,403; and Edwards U.S. Pat. No. 4,263,289. The $\Delta^4$ and $\Delta^{1,4}$ 3-oxoandrostene derivatives of these patents may bear various substituents at the 6, 9, 11 and 16 positions and typically possess a 17α-hydroxy or 17α-alkanoyloxy substituent. The 17β-grouping is variously a carboxylic acid alkyl ester, a carboxylic acid haloalkyl ester or a thiocarboxylic acid alkyl ester. In British Patent Specification No. 1,578,243 and its U.S. counterpart, Kalvoda et al U.S. Pat. No. 4,285,937, there are also described androstadiene-17-carboxylic acids and their esters. The Kalvoda et al compounds are represented in the '937 patent as novel esters of androstadiene 17-carboxylic acids of the formula

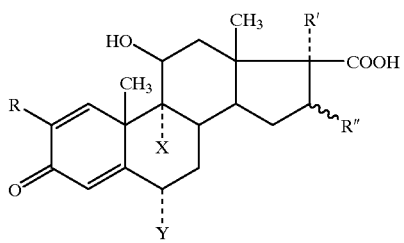

wherein R' represents a free hydroxyl group or a hydroxyl group which is esterified with a carboxylic acid having not more than 7 carbon atoms, R" represents a methyl group in the α- or β- position or the methylene group, R is H or Cl, each of X and Y represents a hydrogen, chlorine or fluorine atom, with the proviso that at least one of these substituents is one of these halogens, when R is Cl, and that Y is only Cl or F and X only Cl, when R is H and that the androstadiene-17-carboxylic acid ester group does not contain more than 11 carbon atoms. These compounds are said to have pronounced anti-inflammatory action coupled with remarkedly low systemic side effects and to be especially suitable for dermatological use. The esters of the steroid 17-carboxylic acids are derived from alcohols containing 1 to 10 carbon atoms of the aliphatic, araliphatic and heterocyclic type which are unsubstituted or substituted by chlorine, fluorine, bromine, hydroxyl, lower alkoxy or lower alkanoyloxy; these alcohols are said to include the lower alkanols (methanol, ethanol, isopropanol etc.). The 17-ester group can also be chloromethoxycarbonyl, fluoromethoxycarbonyl or 2-chloro or 2-fluoroethoxycarbonyl. The esterified hydroxy group R' is said to be derived from a saturated or unsaturated $C_1$–$C_7$ carboxylic acid which is unsubstituted or substituted by halogen atoms, hydroxyl or lower alkoxy groups; named as examples of R' are formyloxy, acetoxy, propionyloxy, butyryloxy, valeryloxy, diethylacetoxy, caproyloxy, chloroacetoxy, chloropropionyloxy, oxypropionyloxy or acetoxypropionyloxy. However, the only specific compound in which the 2-position is unsubstituted which is disclosed by Kalvoda et al is methyl 9α-chloro-6α-fluoro-11β-hydroxy-16α-methyl-3-oxo-17α-propionyloxyandrosta-1,4-diene-17-carboxylate. Indeed, all of Kalvoda et al's specific compounds are 17α-propionyloxy compounds. In view of the fact that Kalvoda et al's compounds are expected to hydrolyze in vivo to release the acid from which the 17α-ester is derived, it is not surprising that the acid preferred by Kalvoda et al for derivatizing the 17α-hydroxyl is propionic acid, which is known to have an $LD_{50}$ in rats of only 4.29 g/kg orally. Acetic acid, which is also basically non-toxic, has an $LD_{50}$ in rats of 3.53 g/kg orally. In contrast, the oral $LD_{50}$ in rats of chloroacetic acid is 76 mg/kg, which is relatively quite toxic.

More recently, soft steroids have been developed in an effort to provide compounds having potent anti-inflammatory activity with minimal systemic activity. These compounds include $\Delta^4$ and $\Delta^{14}$ 17α-alkoxy-11β-hydroxy-3-oxoandrostenes optionally bearing various substituents at the 6,9 and 16-positions and related 11-substituted compounds which are esters or thioesters of 17β-carboxylic acids. These 17α-ethers are described in Bodor U.S. Pat. No. 4,710,495. Preferred compounds are taught to be the haloalkyl esters of 17α-alkoxy-11β-hydroxyandrost-4-en-3-one-17β-carboxylic acids.

Another series of soft steroids which are described as having potent anti-inflammatory activity with minimal systemic activity are the 17α-carbonates of Bodor U.S. Pat. No. 4,996,335. These compounds include as preferred embodiments haloalkyl 17α-alkoxycarbonyloxy-11β-hydroxyandrost-4-en-3-one-17β-carboxylates and the corresponding $\Delta^{14}$ compounds, optionally bearing 6α- and/or 9α-fluorine and 16α- or 16β-methyl substituents. One of these compounds is chloromethyl 17α-ethoxycarbonyloxy-11β-hydroxyandrosta-1,4-dien-3-one-17β-carboxylate, also known as loteprednol etabonate, for which clinical development has been completed and which is awaiting final FDA approval.

Nevertheless, there remains a serious need in this art for new anti-inflammatory steroids which have potent local anti-inflammatory activity while having minimal or non-existent systemic activity.

SUMMARY OF THE INVENTION

The present invention provides new androstene derivatives having anti-inflammatory activity, said derivatives having the structural formula

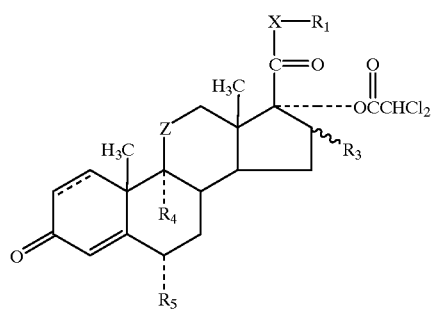

(I)

wherein:
$R_1$ is $C_1$–$C_4$ alkyl, which is unsubstituted or which bears one substituent selected from the group consisting of chloro, fluoro, $C_1$–$C_4$ alkoxy, $C_1$–$C_4$ alkylthio, $C_1$–$C_4$ alkylsulfinyl and $C_1$–$C_4$ alkylsulfonyl;

$R_3$ is hydrogen, α-hydroxy, β-hydroxy, α-methyl, β-methyl, $=CH_2$, or α- or $$\beta\text{—O}\overset{\overset{\displaystyle O}{\|}}{C}CHCl_2;$$

$R_4$ is hydrogen, fluoro or choro;
$R_5$ is hydrogen, fluoro, chloro or methyl;
X is —O— or —S—;
Z is carbonyl, β-hydroxymethylene or β-chloromethylene;
and the dotted line in ring A indicates that the 1,2-linkage is saturated or unsaturated.

Within this group of compounds, the following subgroups are preferred:
(1) compounds in which $R_3$ is H, $R_4$ is H or F and $R_5$ is H, F or $CH_3$;
(2) compounds in which $R_3$ is α-$CH_3$ or β-$CH_3$, $R_4$ is H or F and $R_5$ is H, F or $CH_3$; and
(3) compounds in which $R_3$ is α-OH, β-OH, α-OCOCHCl$_2$ or β-OCOCHCl$_2$, $R_4$ is H or F and $R_5$ is H, F or $CH_3$.

Particularly preferred compounds of the invention are those of formula (I) having one or more of the following structural characteristics:
(1) $R_1$ is unsubstituted $C_1$–$C_4$ alkyl or chloromethyl, especially when $R_1$ is unsubstituted alkyl, most especially when $R_1$ is methyl or ethyl;
(2) X is —O—;
(3) Z is β-hydroxymethylene;
(4) the 1,2-linkage is unsaturated; especially when the $R_3$, $R_4$ and $R_5$ variables are the preferred ones described in the preceding paragraph.

One group of especially preferred derivatives of the invention has the structural formula:

(Ia)

wherein $R_{11}$ is methyl, ethyl, isopropyl or chloromethyl, especially when $R_{11}$ is methyl, ethyl or isopropyl.

The androstene derivatives of formula (I) are extremely potent local anti-inflammatory agents but lack systemic activity. Therefore, the compounds of the present invention can be used in the local (e.g., topical) treatment of inflammatory conditions without the serious systemic side effects which attend use of many known glucocorticosteroids. Moreover, in view of their excellent receptor binding and vasoconstrictor properties, the instant compounds provide a new class of safe and effective steroidal anti-inflammatory agents having an outstanding safety profile.

DETAILED DESCRIPTION OF THE INVENTION

With respect to the various groups encompassed by the generic terms used here and throughout this specification, the following definitions and explanations are applicable:

The alkyl groupings can be straight or branched-chain groups containing the aforementioned number of carbon atoms. Likewise, the alkyl portions of the alkoxy, alkylthio, alkylsulfinyl and alkylsulfonyl groupings each can be straight or branched-chain.

Specific examples of alkyl radicals encompassed by formula (I), whether as specific values for $R_1$ or as a portion of an $R_1$ group, include methyl, ethyl, n-propyl, isopropyl and n-butyl.

The alkoxy, alkylthio, alkylsulfinyl and alkylsulfonyl groupings are of the type
—O-alkyl —S-alkyl
—SO-alkyl
and —SO₂-alkyl, respectively, wherein alkyl is as hereinbefore defined and exemplified.

While all of the compounds encompassed by formula (I) above essentially satisfy the objectives of the present invention, nevertheless certain groups of compounds remain preferred, such as those having the preferred substituents set forth in the Summary of the Invention hereinabove. An especially preferred group of compounds of formula (I) has been set forth in the Summary of the Invention hereinabove as having formula (Ia).

Yet another especially preferred group of compounds consists of the compounds of formula (I) having a 16α-methyl or 16β-methyl substituent, especially those wherein Z, X and $R_1$ are as defined with formula (I) and the remaining structural variables are identical to those in the corresponding positions of dexamethasone, betamethasone, flumethasone or paramethasone, especially when $R_1$ is unsubstituted $C_1$–$C_4$ alkyl or chloromethyl, most especially when $R_1$ is unsubstituted $C_1$–$C_4$ alkyl. Within this group of preferred compounds, those of special interest have the formula:

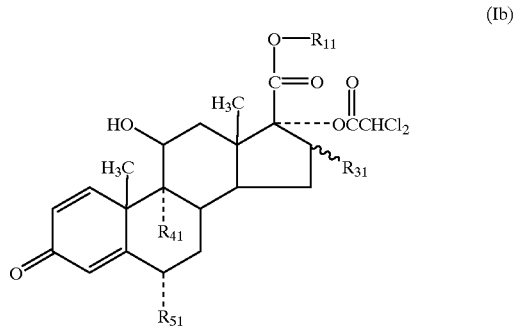

(Ib)

wherein $R_{11}$ is as defined with formula (Ia), $R_{31}$ is α-$CH_3$ or β-$CH_3$, $R_{41}$ is H or F and $R_{51}$ is H or F, particularly when $R_{11}$ is methyl or ethyl.

Another preferred group of compounds consists of the compounds of formula (I) wherein Z, X and $R_1$ are defined as with formula (I) hereinabove and the remainder of the structural variations are identical to those in the corresponding positions of hydrocortisone (i.e., $R_3$, $R_4$ and $R_5$ are each a hydrogen atom and the 1,2-linkage is saturated) or of prednisolone (i.e., $R_3$, $R_4$ and $R_5$ are each a hydrogen atom and the 1,2-linkage is unsaturated), especially when $R_1$ is unsubstituted $C_1$–$C_4$ alkyl or chloromethyl, most especially when $R_1$ is unsubstituted $C_1$–$C_4$ alkyl.

Another preferred group of compounds consists of the 6α- and/or 9α-fluoro congeners of the compounds indicated in the preceding paragraph. Within this group, the compounds wherein Z, X and $R_1$ are defined as with formula (I) and the remaining structural variables are identical to those in the corresponding positions of fluorocortisone, triamcinolone, fluprednisolone, isofluprednone or difluprednate are particularly preferred, especially when $R_1$ is unsubstituted $C_1$–$C_4$ alkyl or chloromethyl, most especially when $R_1$ is unsubstituted $C_1$–$C_4$ alkyl. Yet other interesting compounds are those wherein Z, X, and $R_1$ are defined as with formula (I), $R_3$ is α- or

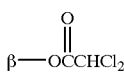

and the remaining structural variables are identical to those in the corresponding positions of triamcinolone, particularly when $R_1$ is unsubstituted $C_1$–$C_4$ alkyl or chloromethyl, most especially when $R_1$ is $C_1$–$C_4$ unsubstituted alkyl.

Yet other androstene derivatives of particular interest herein are the compounds of formula (I) having a 6α-methyl substituent, especially those in which Z, X and $R_1$ are as defined with formula (I) and the remaining structural variables are identical to those in the corresponding positions of fluorometholone or methylprednisolone, especially when $R_1$ is unsubstituted $C_1$–$C_4$ alkyl or chloromethyl, most especially when $R_1$ is unsubstituted $C_1$–$C_4$ alkyl.

In each of the groups of compounds indicated in the three preceding paragraphs, the compounds wherein X is oxygen are particularly preferred. Most especially preferred are the compounds encompassed by the groups indicated above wherein Z is β-hydroxymethylene, wherein X is oxygen, and wherein $R_1$ is unsubstituted $C_1$–$C_4$ alkyl or chloromethyl, especially unsubstituted $C_1$–$C_4$ alkyl (particularly methyl, ethyl or isopropyl).

Although the compounds of formula (I) in which Z is β-hydroxymethylene are generally preferred, particular derivatives in which Z is β-chloromethylene or in which Z is carbonyl are also of considerable interest. These include compounds in which the 1,2-linkage, $R_3$, $R_4$ $R_5$ and Z are identical to the corresponding portions of dichlorisone (in which Z is β-chloromethylene) or in which the 1,2-linkage, $R_3$, $R_4$, $R_5$ and Z are identical to the corresponding portions of prednisone, chloroprednisone or cortisone (in all of which Z is carbonyl). As before, the derivatives of most interest are those in which $R_1$ is $C_1$–$C_4$ unsubstituted alkyl or chloromethyl.

The compounds of formula (I) can generally be prepared by known methods, the method of choice being dependent upon the identity of the various substituents in the desired final product.

One generally useful method for the preparation of the compounds of formula (I) wherein Z is β-hydroxymethylene and X is oxygen utilizes steroidal starting materials of the formula:

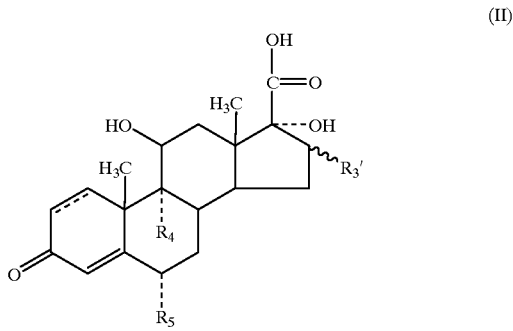

(II)

wherein $R_4$, $R_5$ and the dotted line in ring A are defined as with formula (I) and $R_3'$ is hydrogen, α-methyl, β-methyl, α-OH, β-OH or =$CH_2$ (and which can be conveniently prepared by treatment of the corresponding 21-hydroxypregnenolones of the formula:

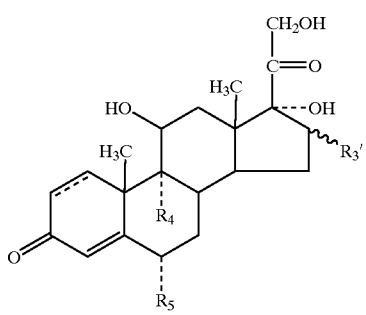

wherein $R_4$, $R_5$, $R_3'$ and the dotted line in ring A are defined as above, with $NaIO_4$ in a suitable organic solvent at room or elevated temperature.) According to this process of the invention, a starting material of formula (II) is reacted with dichloroacetyl chloride ($Cl_2CHCOCl$), under anhydrous conditions, in an appropriate inert organic solvent such as methylene chloride, chloroform or tetrahydrofuran, preferably in the presence of a suitable acid acceptor (e.g., triethylamine, pyridine, calcium carbonate, sodium bicarbonate or other appropriate base). Time and temperature are not critical factors; however, the reaction is conveniently carried out at a temperature between 0° C. and room temperature, for about 1 to 6 hours. The resultant novel 17β-carboxylic acid 17α-dichloroacetate has the formula:

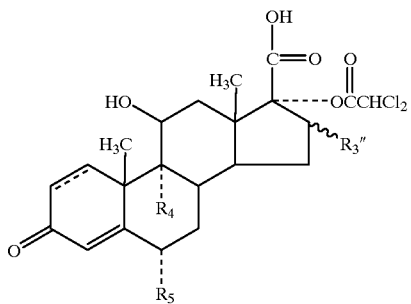

(III)

wherein $R_4$, $R_5$ and the dotted line in the A ring are defined as above and $R_3''$ is H, α-$CH_3$, β-$CH_3$, α-$OCOCHCl_2$, β-$OCOCHCl_2$ or $=CH_2$. When $R_3'$ in the starting material of formula (II) is α-OH or β-OH, sufficient dichloroacetyl chloride is generally employed to ensure formation of the dichloroacetate grouping at the 16-position as well as at the 17-position [i.e., when $R_3'$ in formula (II) is OH, $R_3''$ in the resultant intermediate of formula (III) is α- or β-$OCOCHCl_2$]. If desired, the 16α- or 16β-$OCOCHCl_2$ group can be subsequently removed by selective hydrolysis to regenerate the 16-hydroxy group, for example, by hydrolysis with aqueous sodium bicarbonate solution or treatment with methanolic hydrochloric acid. Alternatively, when a 16α- or β-hydroxy group is present in the starting material, it can be protected by formation of a trimethylsilyl ether or trifluoroacetyl ester, the 16-protected intermediate can then be subjected to the above-described acylation, and the resultant 16-protected 17β-carboxylic acid 17α-dichloroacetate can then be treated in well-known manner to remove the protecting group and provide the corresponding 16-hydroxy 17β-carboxylic acid 17α-dichloroacetate.

When the 17α-substituent is introduced as described in the preceding paragraph, it has been found that purification of the intermediates can be time-consuming because the $R_f$ values of the impurities and the desired intermediates of formula (III) can be very close. However, when the formula (II) starting material is reacted with dichloroacetyl chloride in hexamethylphosphoramide (HMPA) in the presence of silver cyanide, with heating, the desired intermediates can be obtained in high (in some cases, nearly quantitative) yield and with so little impurities that they can be readily purified or can be used in the next step without further purification. The reaction can be conveniently conducted at about 80° C. for a short period of time, for example, on the order of 10 to 15 minutes.

After the above-described introduction of the 17α-substituent, the resultant novel intermediate of formula (III) is readily converted to the corresponding compound of formula (I) by treatment with an alkyl halide $R_1$-Hal [e.g., $CH_3I$, $C_2H_5I$, $(CH_3)_2CHI$], or when $R_1$ is haloalkyl, with a haloalkyl halide [e.g., $ClCH_2I$] or a haloalkyl chlorosulfate Hal-$SO_3R_1$ [e.g., $ClSO_3CH_2Cl$]. When $R_1$ is alkoxy-substituted alkyl or alkylthioalkyl in the final product, an alkoxyalkyl halide or alkylthioalkyl halide can be reacted with the formula (III) intermediate. This step of the reaction sequence can be conveniently conducted at room temperature for about 1 to 24 hours, in an appropriate solvent such as methylene chloride.

The reaction described in the preceding paragraph has been employed using an alkyl halide in sodium bicarbonate in the presence of tetrabutylammonium hydrogen sulfate (TBA) as a phase transfer catalyst, but affords the final products in low overall yield. Moreover, separation of the impurities and desired products is time-consuming. However, when the intermediate of formula (III) is prepared by the silver cyanide process in HMPA, and that intermediate is reacted with an alkyl iodide in the presence of potassium carbonate in HMPA at room temperature, the overall yield is raised significantly, to around 90%. Indeed, nearly quantitative yield can be obtained in the second step when the formula (III) intermediate is used in purified form. The reaction is allowed to run until complete (typically about 1.5 to 2 hours).

The compounds of formula (I) wherein $R_1$ is a sulfinyl- or sulfonyl-containing grouping can be prepared by oxidation of the corresponding thio steroids. Thus, for example, a compound of formula (I) wherein $R_1$ is alkylthioalkyl can be reacted with 1 equivalent of m-chloroperoxybenzoic acid at 0° to 25° C. for 1 to 24 hours, in a suitable solvent such as chloroform, to afford the corresponding compound of formula (I) wherein $R_1$ is alkylsulfinylalkyl, or with 2 equivalents of m-chloroperoxybenzoic acid to afford the corresponding compound of formula (I) wherein $R_1$ is alkylsulfonylalkyl.

When the compounds of formula (I) wherein $R_3$ is α- or β-hydroxy are desired, same can be prepared by partial acid hydrolysis of the corresponding compounds of formula (I) wherein $R_3$ is α- or β-$OCOCHCl_2$, in a suitable solvent medium. Use of a mild reagent, e.g., aqueous sodium bicarbonate solution or oxalic acid in methanol, is desirable. Alternatively, as already noted hereinabove, hydrolysis of the 16-dichloroacetate to the 16-hydroxy compound could be carried out at an earlier stage in the synthetic scheme after the introduction of the 16,17-bis(dichloroacetate) groupings, e.g., selective hydrolysis of an intermediate of formula (III) having 16 and 17 dichloroacetate groupings to the corresponding 16-hydroxy 17-dichloroacetate, followed by conversion to the corresponding compound of formula (I) as described supra.

Another possible process for the preparation of the compounds of the present invention, which can be used to prepare compounds of formula (I) wherein Z is β-hydroxymethylene and X is oxygen or sulfur, utilizes the 17β-carboxylic acid 17α-dichloroacetate intermediates of formula (III) above. According to this process, an intermediate of formula (III) is successively treated, first with a mild acyl chloride forming agent, e.g., such as diethylchlorophosphate or oxalyl chloride, to form the corresponding novel acid chloride of the formula:

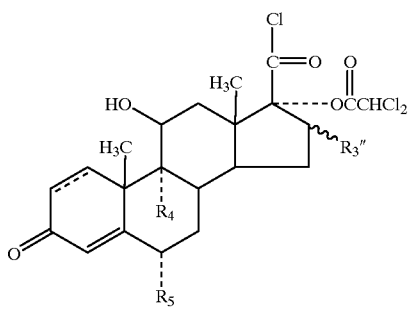

(IV)

wherein $R_3''$, $R_4$, $R_5$ and the dotted line in ring A are defined as above, and then with $R_1XM'$ wherein $R_1$ and X are defined as before, and M' is hydrogen or M wherein M is a suitable metal, e.g., an alkali metal (such as sodium or potassium), alkaline earth metal/2 or thallium or $NH_4$, in an inert solvent (e.g., $CHCl_3$, THF, acetonitrile or DMF), at a temperature between about 0° C. and the boiling point of the solvent, for 1 to 6 hours, to afford the corresponding compound of formula (I). When using a compound of the formula $R_1XM'$ wherein M' is hydrogen, an acid scavenger such as triethylamine is preferably present in the reaction system. The two steps of this process can be very conveniently run in the same solvent, without isolating the acid chloride of formula (IV) formed in the first step. This process is of particular value when a compound of formula (I) wherein X is S is desired.

A halogen exchange reaction based on relative solubilities can be used to convert a chloroalkyl 17β-carboxylate of formula (I) to the corresponding fluoroalkyl derivative. Silver fluoride can be employed in this reaction, which is conducted in a suitable organic solvent (e.g., acetonitrile), and which is especially useful in the preparation of the compounds in which $R_1$ is fluoromethyl or fluoroethyl.

The 21-hydroxypregnenolones from which the steroidal starting materials of formula (II) are prepared can be obtained commercially or prepared by known methods. Likewise, the non-steroidal starting materials used in the various processes discussed above are commercially available or can be prepared by known chemical procedures.

Also, a starting material of formula (II) above can be reacted with dichloroacetyl chloride to afford an intermediate of the formula:

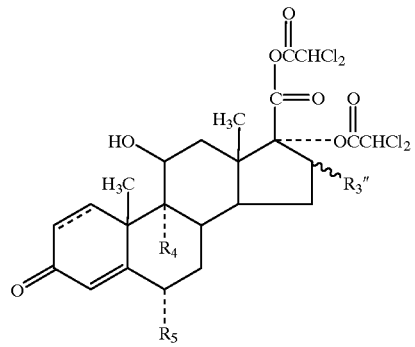

(V)

wherein $R_3''$, $R_4$, $R_5$ and the dotted line in ring A are defined as above, which can be converted to the corresponding intermediate of formula (III) above by partial hydrolysis, with or without isolation of the compound of formula (V). This reaction of a starting material of formula (II) with dichloroacetyl chloride can be carried out under the same conditions as the reaction of a compound of formula (II) with dichloroacetyl chloride as described hereinabove, except that dichloroacetyl chloride is used in an amount of 2 moles or more to one mole of the compound of the formula (II). The partial hydrolysis of the resultant compound of the formula (V) can be carried out in an inert solvent in the presence of a catalyst. Examples of suitable catalysts include tertiary alkyl amines such as triethylamine, trimethylamine or the like; aromatic amines such as pyridine, 4,4-dimethylaminopyridine, quinoline or the like; secondary alkyl amines such as diethylamine, dimethylamine or the like; and inorganic bases such as sodium hydroxide, potassium hydroxide, potassium bicarbonate, or the like. Preferably, pyridine and potassium bicarbonate are employed. Examples of suitable inert solvents for use in the hydrolysis include water; lower alcohols such as ethanol, methanol or the like; ethers such as dimethyl ether, diethyl ether, dimethoxyethane, dioxane, tetrahydrofuran, or the like; halogenated hydrocarbons such as methylene chloride, chloroform or the like; tertiary amines such as pyridine, triethylamine or the like; or a mixture of two or more of the solvents mentioned above. The reaction is usually carried out at a temperature of from about 0 to 100° C., preferably at room temperature to 50° C., for 1 to 48 hours, preferably for 2 to 5 hours.

In yet another aspect, the present invention provides novel compounds of the formula:

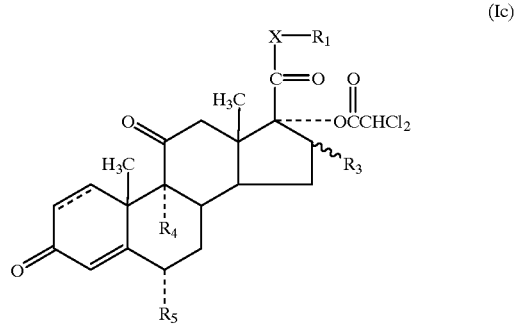

(Ic)

wherein $R_1$, $R_3$, $R_4$, $R_5$, X and the dotted line in ring A are as defined with respect to formula (I) above. The 11-keto compounds of formula (Ic) can be prepared by the procedures described hereinabove for the preparation of the corresponding 11β-hydroxy compounds of formula (I). Thus, a starting material corresponding to formula (II) but having an 11-keto group is reacted with dichloroacetyl chloride to afford the corresponding novel intermediate corresponding to formula (III) or (V), but having an 11-keto group, which can then be reacted as described above for the 11β-hydroxy compounds to ultimately provide a compound of formula (I) in which Z is carbonyl [i.e., a compound of formula (Ic)]. All reaction conditions are as previously described with respect to the corresponding processes for preparing the corresponding 11β-hydroxy compounds of formula (I). Also, the preparation of the compounds of formula (Ic) wherein $R_1$ is a sulfinyl- or sulfonyl-containing grouping or wherein $R_3$ is hydroxy generally proceeds as a final step in the synthetic scheme in a manner analogous to that used for the corresponding 11β-hydroxy compounds of formula (I).

In similar fashion, the compounds of formula (I) in which Z is β-chloromethylene can be readily prepared by methods analogous to those used to prepare the compounds in which Z is β-hydroxymethylene or carbonyl.

In addition, the 11-keto compounds of formula (Ic) can be prepared by reacting the corresponding 11β-hydroxy compounds of formula (I) with an oxidizing agent. The oxidation of an 11β-hydroxy compound of formula (I) in order to convert it into the corresponding compound of formula (Ic) is usually carried out by using an oxidizing agent in an appropriate solvent. The solvent may be any conventional solvent, for example, water, an organic acid (e.g., formic acid, acetic acid, trifluoroacetic acid), an alcohol (e.g., methanol, ethanol), a halogenated hydrocarbon (e.g., chloroform, methylene chloride), or the like. The oxidizing agent may also be any conventional agent which is effective for oxidizing a hydroxy group to a carbonyl group, for example, pyridinium chlorochromate, chromium trioxide in pyridine, hydrogen peroxide, dichromic acid, dichromates (e.g., sodium dichromate, potassium dichromate), permanganic acid, permanganates (e.g., sodium permanganate, potassium permanganate), or the like. The oxidizing agent is usually used in an amount of 1 mole or more, preferably 1 to 3 mole, per mole of the 11β-hydroxy compound of formula (I). The reaction is usually carried out at a temperature of 0 to 40° C., preferably at around room temperature, for about 6 to 30 hours.

The novel compounds of formula (Ic) are useful not only as steroidal anti-inflammatory agents but also as in vivo or in vitro precursors of the corresponding 11β-hydroxy compounds. Thus, the compounds of formula (Ic) can be reduced in vitro to afford the corresponding 11β-hydroxy compounds of formula (I), using a reducing agent known to be capable of reducing the 11-oxo group to an 11β-hydroxy group without modifying the remainder of the steroidal starting material. Typically, microbiological reduction is advantageous for carrying out the desired conversion, although chemical reduction also is possible. Further, the compounds of formula (Ic) may be formulated into appropriate dosage forms (e.g., retention enemas) for the treatment of conditions such as ulcerative colitis. In such dosage forms, it is thought that the compounds of formula (Ic) are microbiologically reduced by bacteria in the body (e.g., in the colon) to the highly active 11β-hydroxy steroids, which elicit the desired anti-inflammatory response.

The preferred compounds of formula (Ic) are those which are precursors of the preferred compounds of formula (I) wherein Z is β-hydroxymethylene. An especially preferred group of compounds of formula (Ic) consists of those compounds wherein X and $R_1$ are defined as above with respect to formula (I) and the remaining structural variations are identical to those in the corresponding positions of cortisone (i.e., $R_3$, $R_4$ and $R_5$ are each a hydrogen atom and the 1,2-linkage is saturated), of prednisone (i.e., $R_3$, $R_4$ and $R_5$ are each hydrogen and the 1,2-linkage is unsaturated), or of the 6α- and/or 9α-fluoro congeners thereof, including 16α-methyl and 16β-methyl compounds such as betamethasone and dexamethasone, particularly when $R_1$ is unsubstituted $C_1$–$C_4$ alkyl or chloromethyl. Most especially preferred of these derivatives are those wherein X is oxygen.

The results of various activity studies of representative species of the invention, discussed in detail below, clearly indicate the potent anti-inflammatory activity and the minimal systemic activity/toxicity of the compounds of formula (I). In view of this desirable therapeutic index, i.e., separation of local and systemic activities, the compounds of the invention can be used in the treatment of topical or other localized inflammatory conditions without causing the serious systemic side effects typically exhibited by the known natural and synthetic glucocorticosteroids such as cortisone, hydrocortisone, hydrocortisone 17α-butyrate, betamethasone 17-valerate, triamcinolone, betamethasone dipropionate and the like. Receptor binding studies, also discussed below, demonstrate that the compounds of the invention have excellent receptor binding properties. Furthermore, human vasoconstrictor testing, also described below, indicates that the instant compounds are potent and long-acting. Other testing has shown that the compounds of formula (I) exhibit a desirable level of stability as well.

While not wishing to be bound by any particular theory, it is believed that the advantageous properties of the compounds of this invention are associated with the manner in which they are metabolized. Despite the hindered nature of the 17α-dichloroacetoxy group, it has been found that, surprisingly, in vivo and in tests in blood, the 17α-group is preferentially and rapidly hydrolyzed to give the 17α-hydroxy-17β-carboxylic acid alkyl ester, which then hydrolyzes to give the non-toxic cortienic acid or congener thereof. This is in contradistinction to the metabolism of simple 17α-alkanoyloxy-17β-carboxylic acid alkyl esters, in which hydrolysis of the 17β-group occurs first, affording a 17α-alkanoyloxy-17β-carboxylic acid, which would be subject to intramolecular group transfer of the acyl moiety to the 17β-position, forming a reactive mixed anhydride according to the scheme:

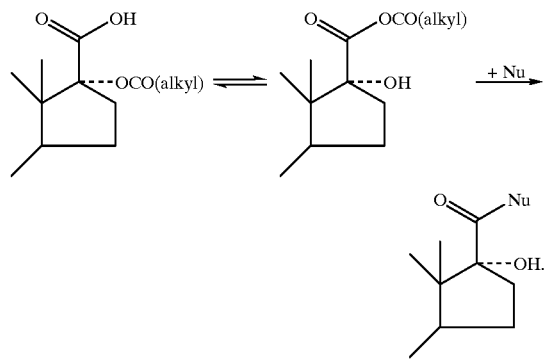

Formation of such reactive intermediates is undesirable since the likely candidates for reaction with this type of reactive intermediate, the plasma proteins, would then be made immunogenic and cause unwanted side effects.

In yet another aspect, the present invention provides new anti-inflammatory steroids having the formula:

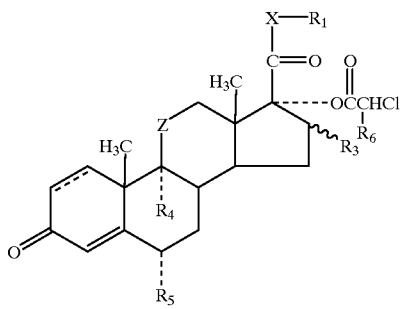

(VI)

wherein $R_6$ is H or $CH_3$ and the remaining structural variables are as defined with formula (I) hereinabove. The compounds of formula (VI) in which $R_6$ is $CH_3$ are generally preferred over those in which $R_6$ is H because the $R_6=CH_3$ compounds usually have greater stability, higher receptor binding affinities and greater local anti-inflammatory activity than the $R_6=H$ compounds.

Within this group of compounds, the following subgroups are preferred:

(1) compounds in which $R_3$ is H, $R_4$ is H or F and $R_5$ is H, F or $CH_3$;

(2) compounds in which $R_3$ is $\alpha$-$CH_3$ or $\beta$-$CH_3$, $R_4$ is H or F and $R_5$ is H, F or $CH_3$; and (3) compounds in which $R_3$ is $\alpha$-OH, $\beta$-OH, $\alpha$-OCOCHCl$_2$ or $\beta$-OCOCHCl$_2$, $R_4$ is H or F and $R_5$ is H, F or $CH_3$.

Especially preferred compounds of formula (VI) have one or more of the following structural characteristics:

(1) $R_1$ is unsubstituted $C_1$–$C_4$ alkyl or chloromethyl; more preferably, $R_1$ is unsubstituted alkyl; most preferably, $R_1$ is methyl or ethyl;

(2) X is —O—;

(3) Z is $\beta$-hydroxymethylene;

(4) the 1,2-linkage is unsaturated; particularly when the $R_3$, $R_4$ and $R_5$ variables are the preferred ones described in the preceding paragraph.

Most especially preferred derivatives of formula (VI) have the structural formulas:

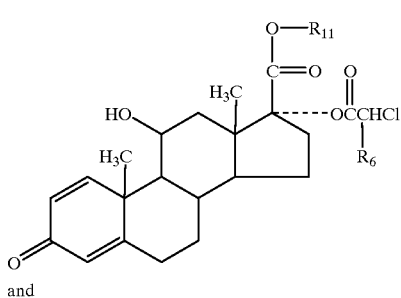

(VIa)

and

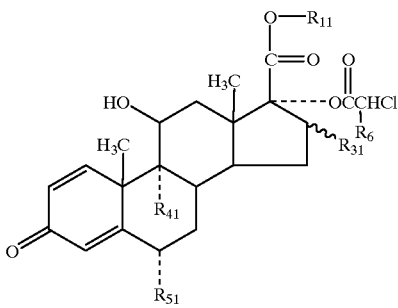

(VIb)

wherein $R_6$ is as defined with formula (VI), $R_{11}$ is methyl, ethyl, isopropyl or chloromethyl, $R_{31}$ is $\alpha$-$CH_3$ or $\beta$-$CH_3$, $R_{41}$ is H or F and $R_{51}$ is H or F, particularly when $R_{11}$ is methyl, ethyl or isopropyl. The especially preferred compounds of formula (VIa) thus share the structural features of prednisolone except at the 17-position. Of the compounds of formula (VIb), those which share the structural features of dexamethasone and betamethasone (wherein $R_{41}$ is F and $R_{51}$ is H) except at the 17-position are especially preferred.

The compounds of formula (VI) can be readily prepared in analogous fashion to the preparation of the compounds of formula (I) discussed above. For example, a starting material of formula (II) can be reacted with the appropriate acyl chloride, ClCH$_2$COCl or ClCH(CH$_3$)COCl, to introduce the desired 17$\alpha$-substituent, then the 17$\beta$-substituent can be introduced by reaction with an alkyl halide, preferably $R_1$I. Process variables are as discussed with respect to the preparation of the compounds of formula (I) above.

EAR EDEMA TEST

In treatment groups of mice, selected amounts of the test compound were dissolved in acetone containing 5% croton oil; then, 50 microliters of the solution were applied to the inner surface of the right ear of each mouse. A control group of mice was identically treated with vehicle only, i.e., 5% croton oil in acetone. Six hours after croton oil challenge, the thickness of each ear was measured. The test results showed an inhibition of swelling of 37.4% and 92.1% at 10 μg/mL and 100 μg/mL doses, respectively, of a representative compound of the invention, i.e., methyl 17$\alpha$-dichloroacetoxy-9$\alpha$-fluoro-11$\beta$-hydroxy-16$\alpha$-methylandrosta-1,4-dien-3-one-17$\beta$-carboxylate. These results were significantly different from control values, p <0.001, and demonstrated that the representative compound of the invention has potent local anti-inflammatory activity.

SKIN WEIGHT TEST

Male Sprague-Dawley rats, weighing about 210 g, were lightly anesthetized with ether, shaved and marked in three areas on each flank with intradermally injected blue ink. Areas on each right flank served as untreated controls, while the areas on each left flank were topically administered 0.1% N,N-dimethylformamide (DMF) solutions of the selected test compound. Treated control animals received daily topical administration of the vehicle (DMF) alone. Solvent and test compound solutions (10 μL) were applied once daily for 10 consecutive days, with reshaving as necessary. On the eleventh day, the animals were sacrificed, their skins were removed and 16 mm diameter plugs were punched out from each area. The plugs were scraped carefully to remove subcutaneous fat and muscle, then they were blotted on filter paper and weighed. The results are presented in TABLE I below. Skin atrophy is a known side effect associated with topically applied anti-inflammatory steroids. The results shown the representative compound, although intrinsically more active than hydrocortisone 17-butyrate, causes less skin atrophy.

steroids on thymi weights in rats when the drugs were systemically administered. In each of these studies, male Sprague-Dawley rats were used. The test compounds were suspended in 0.5% CMC (carboxymethylcellulose) and injected subcutaneously once daily for three days. On the fifth day (48 hours following the last treatment), the animals

TABLE I

Effect on skin weight after 10 days of topical treatment in the rat

| | Daily dose | | No. of | Body wt. | Thymus wt. | Wet skin weight (mg) | | | |
|---|---|---|---|---|---|---|---|---|---|
| Treatment | % | μg | animals | gain (g) | (mg) | Untreated | Decrease %[a] | Treated | Decrease (%) |
| Control | DMF | | 6 | 46.8 ± 2.6 | 480 ± 20 | 83.7 ± 7.0 | | 99.3 ± 2.0 | |
| Methyl 17α-dichloroacetoxy-9α-fluoro-11β-hydroxy-16α-methylandrosta-1,4-dien-3-one-17β-carboxylate | 0.1 | 30 | 4 | 40.8 ± 4.1 | 481 ± 32 | 74.3 ± 4.9 | 11.2 | 87.8 ± 1.7** | 11.6 |
| Hydrocortisone 17-butyrate | 0.1 | 30 | 3 | 45.7 ± 10.6 | 540 ± 61 | 72.0 ± 4.7 | 14.0 | 86.3 ± 1.5** | 13.1 |
| Clobetasol 17-propionate | 0.1 | 30 | 5 | 24.2 ± 2.3*** | 190 ± 14*** | 67.6 ± 6.2 (Mean ± S.E.) | 19.2 | 78.2 ± 2.3*** | 21.2 |

[a] Values expressed as a percent decrease of the control.
Significantly different from the control group: *, $p < 0{,}05$; , $p < 0.01$; *, $p < 0.001$.

GRANULOMA FORMATION TEST

The test compound was dissolved in acetone and aliquots of varying concentrations were injected into cotton pellets. The pellets were dried and then one pellet was implanted beneath the skin of each test rat. Six days later, the animals were sacrificed and the granulation tissue (granuloma) which formed in and around the implanted pellet was removed, dried and weighed. In addition, the thymi and adrenals were removed and weighed. The ability of a compound to inhibit granuloma formation in this test is a direct indication of local anti-inflammatory activity; thus, the lower the weight of granulation tissue, the better the anti-inflammatory activity. On the other hand, a significant decrease in thymus weight is indicative of significant systemic activity; conversely, when a test compound does not significantly decrease thymus weight as compared to the control, such is indicative of a lack of (or very minimal) systemic side effects.

When tested in this manner, a representative compound of the invention, namely methyl 17α-dichloroacetoxy-9α-fluoro-11β-hydroxy-16α-methylandrosta-1,4-dien-3-one-17β-carboxylate, exhibited significant local anti-inflammatory activity while having a relatively much lower systemic effect.

From the results obtained in the test described above, the $ED_{50}$'s and the relative potencies of a representative compound of the invention and prior art steroids were calculated and are shown in TABLE II below. One of the prior art steroids, namely betamethasone valerate, has been assigned a potency value of 100 at the $ED_{50}$ level, and the potencies of the other compounds are expressed relative thereto. The $ED_{50}$'s are the dosages required to achieve 50% reduction in the weight of the granulation tissue.

THYMUS INHIBITION TESTING

Several further studies were undertaken to determine the effects of a selected compound of the invention and prior art were sacrificed and the thymi weights were recorded. Body weight gains were measured 24 hours after the last treatment. From the test results, the $TED_{40}$'s (thymolytic effective doses, that is, doses required to achieve 40% inhibition of thymi weight) and relative potencies of a representative compound of the invention and reference steroids were calculated. In TABLE II below, the relative potency for the reference steroid betamethasone 17-valerate at the $TED_{40}$ dose has been assigned a value of 100, and the potencies of the other compounds are expressed relative thereto. It is evident that the higher the inhibition of thymus activity at a given dose, the more toxic the compound is.

The $ED_{50}$'s calculated for the local cotton pellet granuloma assay and the $TED_{40}$'s calculated on the basis of thymus inhibition testing as described above were used to arrive at relative potency and a therapeutic index for a representative species of the invention as compared to prior art steroids. See TABLE II below, which clearly shows the potent anti-inflammatory activity and minimal systemic toxicity of the representative compound of the present invention.

TABLE II

Comparison of local effect and systemic side-effects

| Test Compound | Granuloma Relative Potency at $ED_{50}$ level (a) | Thymolysis Relative Potency at $ED_{40}$ Level (b) | Therapeutic Index (a/b) |
|---|---|---|---|
| Methyl 17α-dichloroacetoxy-9α-fluoro-11β-hydroxy-16α methylandrosta-1,4-dien-3-one-17β-carbonylate | 1107 | 156 | 7.10 |
| Hydrocortisone 17-butyrate | 70 | 57 | 1.23 |
| Clobetisol 17-propionate | 2965 | 1927 | 1.54 |
| Betamethasone valerate | 100 | 100 | 1.0 |

Additional representative compounds of the invention were subjected to a variety of stability and receptor binding studies as well as to human vasoconstriction testing, as described in detail below.

STABILITY STUDIES

Analytical Method

A high performance liquid chromatographic (HPLC) method was developed for the quantitative determination of the following compounds of the invention:

| Test Compound | Chemical Name |
|---|---|
| A | Methyl 17α-dichloroacetoxy-11β-hydroxyandrosta-1,4-dien-3-one-17β-carboxylate |
| B | Ethyl 17α-dichloroacetoxy-11β-hydroxyandrosta-1,4-dien-3-one-17β-carboxylate |
| C | Isopropyl 17α-dichloroacetoxy-11β-hydroxyandrosta-1,4-dien-3-one-17β-carboxylate |
| D | Chloromethyl 17α-dichloroacetoxy-11β-hydroxyandrosta-1,4-dien-3-one-17β-carboxylate |

These are preferred compounds of the invention having formula (Ia) set forth earlier in this description.

A Whatman C-18 column (4.6 mm×108 mm) was connected to a Spectra-Physics component system consisting of a SP 8810 precision isocratic pump, Rheodyne 7125 injector (20 μL injection volume), SP 8450 UV/VIS variable wavelength detector (230 nm), and SP 4290 integrator. The system was operated at ambient temperature. The mobile phase consisted of acetonitrile, acetic acid and water (60:0.1:40). At a flow rate of 1.0 mL/minute, the retention times for the test compounds were 4.74 minutes for Compound A, 5.84 minutes for Compound B, 6.93 minutes for Compound C, and 5.72 minutes for Compound D.

HPLC peak area and peak height were used as a measure of the concentration of the test compounds and plotted against time to evaluate the disappearance rates of the compounds. The stability was determined by measuring the pseudo-first order rate constant ($k_{obs}$ in min$^{-1}$) or half-life ($t_{1/2}$ in min) of disappearance of the test compound in buffer. The $k_{obs}$ was determined from the slope of the log of the disappearance curve [$k_{obs}$=slope×(−2.303)] and the $t_{1/2}$ of the test compound was calculated from the equation $t_{1/2}$=0.693/$k_{obs}$.

Stability in Buffers

The stabilities of test compounds A, B, C, and D, were tested in buffer solutions in the pH range of 4.0 to 9.0. A 0.1 mL portion of each compound at a concentration of 1 mM was mixed with 10 mL phosphate buffer (made by combining 0.05 M of NaH$_2$PO$_4$ and 0.05 M of Na$_2$HPO$_4$ with 0.05 M of NaCl) to give a final concentration of 0.01 mM. The mixtures were incubated at 37° C., and samples were taken and injected in the HPLC system at appropriate time intervals. pH profiles of each test compound are shown in TABLE III below.

TABLE III

Stability, half-life ($t_{1/2}$, min), of test compounds in aqueous phosphate buffer solution (pH 7.40) at 37° C.

| Compound of Formula (Ia) | | Half-life (minutes) at indicated pH levels | | | | |
|---|---|---|---|---|---|---|
| No. | $R_{11}$ | 4.50 | 6.56 | 7.40 | 8.08 | 9.00 |
| A | CH$_3$ | * | 1146 | 202 | 21.0 | 4.25 |
| B | CH$_2$CH$_3$ | * | 1004 | 305 | 52.0 | 8.67 |

TABLE III-continued

Stability, half-life ($t_{1/2}$, min), of test compounds in aqueous phosphate buffer solution (pH 7.40) at 37° C.

| Compound of Formula (Ia) | | Half-life (minutes) at indicated pH levels | | | | |
|---|---|---|---|---|---|---|
| No. | $R_{11}$ | 4.50 | 6.56 | 7.40 | 8.08 | 9.00 |
| C | CH(CH$_3$)$_2$ | * | 680 | 974 | 125 | 16.2 |
| D | CH$_2$Cl | 841 | 49.3 | 13.9 | 2.9 | 1.07 |

*No degradation observed in two days.

Stability in Biological Media

A 0.2 mL aliquot of stock solution (1 mM) of each of the test compounds A, B, C, and D, was added to 2 mL of each biological media (whole heparinized rat blood, 20% rat liver homogenate, and 6-volume diluted lung homogenate in isotonic buffer of pH 7.40 made by combining 0.05 M of Na$_2$HPO$_4$ and 0.05 M of NaH$_2$PO$_4$ with 0.05 M of NaCl), which was kept in a 37° C. water bath, to obtain a final concentration of 0.1 mM in each biological medium. Samples of 0.1 mL were taken at appropriate time intervals for 2 hours (at 0, 3, 5, 10, 20, 40, 60, 90 and 120 minutes) and mixed with 0.2 mL of acetonitrile containing 5% DMSO. Each mixture was centrifuged and the supernatant was injected in the HPLC. The stabilities ($t_{1/2}$, half-lives) of the test compounds in rat blood, liver homogenate, and lung homogenate are shown in TABLE IV below.

TABLE IV

Stability, half-life ($t_{1/2}$ min), of test compounds in aqueous phosphate buffer solution (pH 7.40) and various biological media at 37° C.

| Compound of Formula (Ia) | | Half-life (minutes) | | | |
|---|---|---|---|---|---|
| No. | $R_{11}$ | Buffer | Blood | Liver | Lung |
| A | CH$_3$ | 201.9 | 26.9 | 3.70 | 43.1 |
| B | CH$_2$CH$_3$ | 304.8 | 77.4 | 18.8 | 137.2 |
| C | CH(CH$_3$)$_2$ | 657.6 | 106.9 | 29.3 | 170.4 |
| D | CH$_2$Cl | 13.9 | 11.6 | 7.60 | 52.4 |

Stability in Cytosol

To determine that the compounds of the invention can be stable during the incubation period, the test compounds A, B, C, and D were investigated for their stabilities at the incubation conditions, which are room temperature and 2 hours, for receptor binding studies. The frozen cytosol which was made for the receptor binding study was thawed in a water bath and diluted with 1 part of incubation buffer (10 mM Tris/HCl, 10 mM sodium molybdate, and 2 mM 1,4-dithiothreitol) containing a 15 mM concentration of enzyme inhibitor, diisopropyl fluorophosphate. Portions (560 μL) of the diluted cytosol were added to centrifuge tubes containing 80 μL portions of blank incubation buffer instead of volume of tracer ([$^3$H]triamcinolone acetonide) which would be used in the receptor binding study (RBS), 80 μL of solution of a Δ$^1$-cortienic acid (0.1 mM) in buffer (the final concentration of Δ$^1$-cortienic acid in the incubation medium was 10 nM), and 80 μL of 100,000 nM of concentrations of test compounds in ethanol to give a final concentration of 10,000 nM. This mixture was kept at room temperature for 2 hours. Samples of 0.1 mL were taken at appropriate time intervals (0, 0.5, 1, 1.5, 2 hours) and were mixed with 0.2 mL of acetonitrile containing 5% DMSO.

Each mixture was centrifuged and the supernatant were injected in the HPLC. The stabilities (% remaining after incubation) of the test compounds in cytosol at different conditions are shown in TABLE V.

TABLE V

Stability of test compounds in the incubation medium

| Compound of Formula (Ia) | | % remaining after 2 hour |
|---|---|---|
| No. | $R_{11}$ | incubation |
| A | $CH_3$ | 75.1 |
| B | $CH_2CH_3$ | 100 |
| C | $CH(CH_3)_2$ | 100 |
| D | $CH_2Cl$ | 70.6 |

FURTHER STABILITY AND METABOLISM STUDIES

Analytical Method

A high performance liquid chromotographic (HPLC) method operated at ambient temperature was developed for the determination of the following compounds:

(VII)

| Compound of Formula (VII) | $R_{13}$ | $R_{23}$ | $R_{33}$ | $R_{43}$ |
|---|---|---|---|---|
| B | $CH_2CH_3$ | $COCHCl_2$ | H | H |
| F | $CH_2CH_3$ | H | H | H |
| H | H | $COCHCl_2$ | H | H |
| I | $CH_3$ | $COCHCl_2$ | $CH_3$ | F |
| J | $CH_2CH_3$ | $COCHCl_2$ | $CH_3$ | F |
| L | H | $COCHCl_2$ | $CH_3$ | F |
| M | $CH_2CH_3$ | H | $CH_3$ | F |
| N | H | $COCHCl_2$ | $CH_3$ | F |
| O | $CH_3$ | H | $CH_3$ | F |

A Waters NOVA-PAK phenyl column was connected to a Spectra-Physics component system consisting of a SP 8810 precision isocratic pump, a Rheodyne 7125 injector (injection volume 20 µL), an SP 8450 UV/VIS variable wavelength detector (operated at 254 nm) and a SP 4270 integrator. The mobile phase consisted of acetonitrile, water and acetic acid at a volume ratio of 40:60:0.1, operated at a flow rate of 1 mL/minute. The retention times of compound of the invention B and its metabolites F and H were 6.32, 2.25 and 1.66 minutes, respectively. The retention times of compound of the invention J and its metabolites L and M were 8.64, 2.70 and 2.45 minutes, respectively. The retention times of compound of the invention I and its metabolites N and O were 5.84, 2.70 and 1.81 minutes, respectively. The retention time of cortienic acid was 1.00 minute.

Stability in Human or Rat Plasma

Freshly collected human or rat plasma was used. An aliquot of 10 mM test compound in ethanol solution was added to prewarmed (37° C.) plasma to yield a final concentration of 100 µM. At appropriate time intervals, samples (0.1 mL) were removed and mixed with 0.2 mL of 5% dimethylsulfoxide/acetonitrile solution. Mixtures were centrifuged and supernatants were analyzed by HPLC. The pseudo-first order rate constant of the disappearance of compound in the biological media was determined by linear regression analysis from the plot of log peak area and peak height versus time.

Stability was evaluated by the pseudo first-order rate constant (k, hr$^{-1}$) and half-life (t$_{1/2}$, hr) of the disappearance of the test compound in the media. Results are summarized in TABLES VI and VII below.

TABLE VI

Stability of compounds of the invention in human plasma at 37° C.

| Test Compound | k, hr$^{-1}$ | t½, hr | r |
|---|---|---|---|
| B | 0.138 | 5.03 | 0.970 |
| I | 0.0633 | 10.94 | 0.994 |
| J | 0.0173 | 40.11 | 0.989 |

TABLE VII

Stability of compounds of the invention in rat plasma at 37° C.

| Test Compound | k, hr$^{-1}$ | t½, hr | r |
|---|---|---|---|
| B | 0.136 | 5.08 | 0.999 |
| I | 0.0702 | 9.88 | 0.999 |
| J | 0.0170 | 40.73 | 0.996 |

The kinetic data generated by following the disappearance of the compounds of the invention by HPLC showed formation of all of the expected metabolites, i.e. the corresponding compounds of formula (VII) in which $R_{13}$ is H (H, L, N) and those in which $R_{23}$ is H (F, M, O), as well as the ultimate metabolites in which $R_{13}$ is H and $R_{23}$ is H (cortienic acid and the corresponding 9α-fluoro-16α-methyl acid).

RECEPTOR BINDING STUDIES

Materials

Unlabeled chemicals were obtained from Sigma Chemical Co. (St. Louis, MO.). The radiolabelled compound, 1,2,4-[$^3$H]-triamcinolone acetonide (45 Ci/mmol) was purchased from New England Nuclear (Boston, Mass.). Solvents for the mobile phases were of HPLC grade which was ACS certified.

Apparatus

For the receptor binding assays, the following were used: T line Laboratory homogenizer (Talboys Engineering Corp., Emerson, N.J.); Virtis 45 homogenizer (The Virtis Co., Gardiner, N.Y.); Beckman L8-70 M Ultracentrifuge with T-170 Rotor (Palo Alto, Calif.); Fischer Micro Centrifuge, Model 235 C (Fischer Scientific Co., Fairlawn, N.J.); Beckman LS 500 TD, Liquid Scintillation Counter (Fullerton, Calif.).

Preparation of the Cytosol

Male Sprague-Dawley rats, each weighing 150 to 200 g, were used 6 days after adrenalectomy. Rats were sacrificed by decapitation. Immediately after resection of the lungs, the tissue was frozen in ice. The cytosol was prepared using a slight modification of a previously described method (Dahlberg, 1984); After addition of 6 volumes of ice-cold incubation buffer (10 mM Tris/HCl, 10 mM sodium molybdate, and 2 mM 1,4-dithiothreitol), the tissue was homogenized with the Virtis 45 homogenizer at full speed, for 4 periods of 10 seconds with a 10-second cooling period between each step. The homogenate was centrifuged at 35,000 g for 1 hour at 4° C. in a Beckman ultracentrifuge L8-70M equipped with a T170 rotor. Portions (5 ml) of the cytosol were frozen in liquid nitrogen and stored at −80° C.

Binding Studies

The following compounds of the invention A, B, C and D, and their putative metabolites E, F, G and H were investigated in these studies:

(VIII)

Compound of Formula (VIII)

| | $R_{12}$ | $R_{22}$ |
|---|---|---|
| A | $CH_3$ | $COCHCl_2$ |
| B | $CH_2CH_3$ | $COCHCl_2$ |
| C | $CH(CH_3)_2$ | $COCHCl_2$ |
| D | $CH_2Cl$ | $COCHCl_2$ |
| E | $CH_3$ | H |
| F | $CH_2CH_3$ | H |
| G | $CH(CH_3)_2$ | H |
| H | H | $COCHCl_2$ |

The representative compounds of the invention (A, B, C, and D), their metabolites (E, F, G, and H), dexamethasone, and triamcinolone acetonide were each dissolved in absolute ethanol to give 1 mM concentration and diluted to obtain various concentrations in the range of 300,000 nM to 10 nM with 40% of ethanol in water. The cytosol was thawed in a water bath and diluted with 1 part of incubation buffer containing a 15 mM concentration of diisopropyl fluorophosphate. Portions (140 µL) of the diluted cytosol were added to centrifuge tubes containing 20 µL portions of a stock solution of [$^3$H]triamcinolone acetonide in incubation buffer (the final concentration of tracer in each incubation medium being 10 nM), 20 µL of solution of $\Delta^1$-cortienic acid (0.1 mM) in buffer (the final concentration of $\Delta^1$-cortienic acid in the incubation medium being 10 nM), and 20 µL of various concentrations of competitor (compounds of the invention A, B, C, and D; their metabolites, E, F, G, and H; dexamethasone; and triamcinolone acetonide) in ethanol. After a 2 hour incubation period at room temperature (24° C.), the unbound steroid was removed by addition of a 2% suspension of activated charcoal in incubation buffer (400 µL). The mixture was incubated for 5 minutes at room temperature and then was centrifuged at about 10,000 g for 3 minutes in the microcentrifuge. The radioactivity (cpm) in the supernatant (400 µL) was determined by liquid scintillation counting. The non-specific binding was determined in the presence of unlabeled dexamethasone ($10^{-6}$) and was in all cases less than 10% of the total binding.

The $IC_{50}$ value of the investigated steroid (concentration of competitor necessary to displace 50% of the bound [$^3$H]triamcinolone acetonide) and the slope factor of the resulting competition curve were determined by a non-linear curve fitting method using the NON-LIN module of the Macintosh SYSTAT version. The data is fitted to the following logistic function:

$$B=T-T * C^N/(C^N+IC_{50}{}^N)+NS,$$

where B=CPM in the presence of competitor, T=CPM in the absence of competitor, C=competitor concentration, N=Hill slope factor, and NS=cpm under non-specific binding conditions. The resulting $IC_{50}$ value was transformed into relative binding affinity (RBA) using dexamethasone (RBA=100) as the reference standard:

$$RBA(X)=IC_{50} \text{ (dexamethasone)}/IC_{50}(X) * 100.$$

The receptor binding affinities (RBAs) of representative compounds of the invention A, B, C, and D, and their putative metabolites, E, F, G, and H for the rat lung glucocorticoid receptor are shown in TABLE VIII below.

TABLE VIII

Relative binding affinities (RBAs) of test compounds

| Test Compound | $IC_{50}$ | RBA[a] |
|---|---|---|
| A | 49.45 | 165 |
| B | 40.06 | 204 |
| C | 69.77 | 117 |
| D | 11.93 | 684 |
| E | >2000 | <1 |
| F | >2000 | <1 |
| G | >2000 | <1 |
| H | >2000 | <2 |
| Dexamethasone | 81.61 | 100 |
| Triamcinolone acetonide | 13.00 | 628 |

[a]Relative binding affinity with respect to dexamethasone (RBA = 100).

Another representative compound of the invention, methyl 17α-dichloroacetoxy-9α-fluoro-11β-hydroxy-16α-methylandrosta-1,4-dien-3-one-17β-carboxylate, has been found to have a RBA of 495 when tested in this manner. Loteprednol etabonate has been previously found to have an RBA of 420. In contrast, it has been found that compounds of formula (VI) in which $R_{12}$ is ethyl and $R_2$ is lower alkanoyl, i.e., the well-known alkyl 17α-alkanoyloxy-17β-carboxylate analogs of the compounds of this invention have RBAs of less than 1.

Effect of $\Delta^1$-cortienic acid on the Receptor Binding Affinities

For the representative compound of the invention B, receptor binding affinity was investigated with and without $\Delta^1$-cortienic acid in the incubation solution to study the effect of $\Delta^1$-cortienic acid on the receptor binding. The results are shown in TABLE IX below.

TABLE IX

Comparison of receptor binding affinities (RBAs) between "with" and "without" $\Delta^1$-cortienic acid in receptor binding study of Compound B

| Condition | Receptor binding affinity |
|---|---|
| With $\Delta^1$-cortienic acid | 204 |
| Without $\Delta^1$-cortienic acid | 181 |

Loteprenol etabonate has been previously found to have an RBA without $\Delta^1$-cortienic acid of 152, while its RBA with $\Delta^1$-cortienic acid has been found to be 420. Unlike loteprednol etabonate, the present compounds do not bind to transcortin. Consequently, the instant compounds are more available to the desired enzymatic deactivation, which in turn further enhances their lack of unwanted side-effects.

FURTHER RECEPTOR BINDING STUDIES

Further studies to evaluate the relative receptor binding affinities of compounds of the invention, other compounds of formula (VII) hereinabove and well-known anti-inflammatory steroids were undertaken, using the methods described in the RECEPTOR BINDING STUDIES set forth above. The well-known steroids tested were dexamethasone, triamcinolone acetonide, fluorometholone and betamethasone 17-valerate. The compounds of the invention tested were compounds A, B, C, D, I and J as set forth above. For comparison purposes, the following compounds having formula (VII) above were also tested:

| Compound of Formula (VII) | $R_{13}$ | $R_{23}$ | $R_{33}$ | $R_{43}$ |
|---|---|---|---|---|
| P | $CH_2CH_3$ | $COCH_2CH_3$ | H | H |
| Q | $CH_2CH_3$ | $COCHClCH_3$ | H | H |
| R | $CH_2CH_3$ | $COCH_2Cl$ | H | H |

The results are presented in TABLE X below.

TABLE X

Relative receptor binding affinities (RBAs) of test compounds

| Test Compound | RBA | % left after incubation |
|---|---|---|
| Dexamethasone | 100 | |
| Triamcinolone acetonide | 630 | |
| Fluorometholone | 136 ± 5* | |
| Betamethasone 17-valerate | 1742 ± 130* | |
| A | 165 | 75% |
| B | 222 ± 16* | 75% |
| C | 117 | >90% |
| D | 684 | 70% |
| I | 1745 ± 185* | >90% |
| J | 687 ± 49* | >90% |
| P | 38 | >90% |
| Q | 88 | >90% |
| R | 22 | 30% |

*mean ± SE of 3–5 results.

HUMAN VASOCONSTRICTION TEST

Test compounds (10 mM) were dissolved in ethanol/propylene glycol (9/1) solution, and 50 µL of the mixtures were applied to circular patches, 8 mm in diameter. After ethanol evaporation, the patches were applied to the forearm of a human volunteer, and covered with a water impervious film for 3 hours. The intensity of vasoconstriction was judged 1, 8, 17 and 24 hours after the patches were removed.

The grading scale for the vasoconstriction activity was as follows: 0, normal skin; 1, slight pallor of indistinct outline; 2, pallor with at least two corners outlined; 3, even pallor with a clear outline of the application sites; 4, very intense pallor.

TABLE XI

Vasoconstriction activity of dexamethasone, loteprednol etabonate and various compounds of formula (Ia)

| Time (hour) | 1 | 8 | 17 | 24 |
|---|---|---|---|---|
| Dexamethasone-Sample 1 | 0 | 1 | 1 | 1 |
| Dexamethasone-Sample 2 | 0 | 1 | 1 | 1 |
| Loteprednol etabonate-Sample 1 | 2 | 3 | 2 | 2 |
| Loteprednol etabonate-Sample 2 | 2 | 2 | 2 | 1 |
| A | 2 | 4 | 4 | 4 |
| B-Sample 1 | 3 | 4 | 4 | 4 |
| B-Sample 2 | 3 | 4 | 4 | 4 |
| C | 3 | 4 | 3 | 2 |
| D-Sample 1 | 3 | 4 | 3 | 2 |
| D-Sample 2 | 3 | 4 | 3 | 2 |

Since the degree of pallor depends both on the intrinsic potency of the test compound and on the amount of compound reaching its site of action, one can conclude that the representative compounds of this invention are potent and long-acting topical anti-inflammatory agents with good permeation properties.

FURTHER HUMAN VASOCONSTRICTION TESTING

Method 1

Test compounds (0.1–10 mM) were dissolved in ethanol/propylene glycol (9/1) solution to obtain a clear mixture. The mixtures, in 50 µL amounts, were applied to circular patches (8 mm diameter). After evaporation of ethanol, the patches were applied to the forearms of a human volunteer, and covered with a water impervious film for 3 hr. The intensity of vasoconstriction (scale 0–4) was judged at various time intervals after removal of the patches. The grading scale was as follows: 0, normal skin; 1, slight pallor of indistinct outline; 2, pallor with at least two corners outlined; 3, even pallor with a clear outline of the application sites; 4, very intense pallor. The skin tests (2–4 tests on each compound) were performed on the same person. Results are listed in TABLES XII and XIII below.

Method 2

Test compounds (0.1–5 mM) were dissolved in ethanol/propylene glycol (9/1) solution. The mixtures, in 20 µL amounts, were applied to circular patches (¼ inch diameter). The patches were applied to the forearm of a human volunteer, and covered with a water impervious film for 3 hr. Vasoconstriction activity was judged by the appearance of pallor at various time points after the patches were removed. Tests were performed on the same person and the results were obtained from 2–4 observations. Results are listed in TABLE XIV below.

Dexamethasone, betamethasone 17-valerate and loteprednol etabonate were used as reference compounds for comparison purposes. The following compounds of formula (VII) above were also tested:

| Compound of Formula (VII) | $R_{13}$ | $R_{23}$ | $R_{33}$ | $R_{43}$ |
|---|---|---|---|---|
| A | $CH_3$ | $COCHCl_2$ | H | H |
| B | $CH_2CH_3$ | $COCHCl_2$ | H | H |
| C | $CH(CH_3)_2$ | $COCHCl_2$ | H | H |
| D | $CH_2Cl$ | $COCHCl_2$ | H | H |
| I | $CH_3$ | $COCHCl_2$ | $CH_3$ | F |
| J | $CH_2CH_3$ | $COCHCl_2$ | $CH_3$ | F |
| K | $CH_2Cl$ | $COCHCl_2$ | $CH_3$ | F |
| P | $CH_2CH_3$ | $COCH_2CH_3$ | H | H |
| Q | $CH_2CH_3$ | $COCHClCH_3$ | H | H |
| R | $CH_2CH_3$ | $COCH_2Cl$ | H | H |

-continued

| Compound of Formula (VII) | $R_{13}$ | $R_{23}$ | $R_{33}$ | $R_{43}$ |
|---|---|---|---|---|
| S | $CH_3$ | $COCH_2Cl$ | $CH_3$ | F |
| T | $CH_2CH_3$ | $COCH_2Cl$ | $CH_3$ | F |

Compounds A, B, C and D are compounds of the invention of formula (Ia). Compounds I, J and K are compounds of the invention of formula (Ib). Compound P is a 17α-non-halogenated alkanoyloxy compound selected for comparison purposes. Compounds Q, R, S and T are 17α-monohalogenated alkanoyloxy compounds of formula (VI) hereinabove.

TABLE XII

Vasoconstriction activity after 3 and 20 hours (Method 1)

| Test Compound | Concentration, mM | | | | | | |
|---|---|---|---|---|---|---|---|
|  | 10 | 5 | 1 | 0.5 | 0.1 | 0.05 | 0.01 |
| 3 Hours |  |  |  |  |  |  |  |
| Dexamethasone | 1 | — | — | — | — | — | — |
| Betamethasone 17-valerate | 4 | 3 | 3 | 2 | 1 | 1 | 0 |
| Loteprednol etabonate | 4 | 3 | 3 | 2 | 1 | 0 | 0 |
| A | 4 | — | — | — | — | — | — |
| B | 4 | 3 | 3 | 2 | 1 | 1 | 0 |
| C | 4 | — | — | — | — | — | — |
| D | 4 | — | — | — | — | — | — |
| I | 4 | 4 | 4 | 3 | 2 | 2 | 1 |
| J | 4 | 3 | 3 | 2 | 2 | 1 | 0 |
| K | — | — | — | — | — | — | — |
| P | — | 3 | 2 | 1 | 0 | 0 | 0 |
| Q | — | 3 | 1 | 1 | 0 | 0 | 0 |
| R | — | 1 | 1 | 1 | 0 | 0 | 0 |
| 20 Hours |  |  |  |  |  |  |  |
| Dexamethasone | 1 | — | — | — | — | — | — |
| Betamethasone 17-valerate | 2 | 1 | 1 | 1 | 1 | 1 | 0 |
| Loteprednol etabonate | 2 | 1 | 0 | 0 | 0 | 0 | 0 |
| A | 2 | — | — | — | — | — | — |
| B | 2 | 1 | 1 | 1 | 1 | 0 | 0 |
| C | 1 | — | — | — | — | — | — |
| D | 1 | — | — | — | — | — | — |
| I | — | 2 | 1 | 1 | 1 | 1 | 0 |
| J | 2 | 1 | 1 | 1 | 0 | 0 | 0 |
| K | — | — | — | — | — | — | — |
| P | — | 1 | 1 | 0 | 0 | 0 | 0 |
| Q | — | 1 | 1 | 1 | 0 | 0 | 0 |
| R | — | 0 | 0 | 0 | 0 | 0 | 0 |

TABLE XIII

Vasoconstriction activity after 24 hours with 1 hour re-occlusion at 20–21 hours (Method 1)

24 Hours

| Test Compound | Concentration, mM | | | |
|---|---|---|---|---|
|  | 0.5 | 0.1 | 0.05 | 0.01 |
| Betamethasone 17-valerate | 2 | 2 | 1 | 1 |
| B | 2 | 2 | 1 | 1 |
| I | 3 | 3 | 2 | 1 |
| J | 2 | 2 | 1 | 1 |
| P | 2 | 1 | 0 | 0 |

TABLE XIII-continued

Vasoconstriction activity after 24 hours with 1 hour re-occlusion at 20–21 hours (Method 1)

24 Hours

| Test Compound | Concentration, mM | | | |
|---|---|---|---|---|
|  | 0.5 | 0.1 | 0.05 | 0.01 |
| Q | 2 | 1 | 0 | 0 |
| R | 0 | 0 | 0 | 0 |

TABLE XIV

Vasoconstriction activity determined using Method 2 at various time points

| Test Compound | Concentration, mM | | | | | |
|---|---|---|---|---|---|---|
|  | 5 | 1 | 0.5 | 0.1 | 0.05 | 0.01 |
| 4 Hours |  |  |  |  |  |  |
| I | + | + | + | + | − | − |
| J | + | + | − | − | − | − |
| K | + | + | − | − | − | − |
| S | − | − | − | − | − | − |
| T | − | − | − | − | − | − |
| Betamethasone 17-valerate | + | + | − | − | − | − |
| 8 Hours |  |  |  |  |  |  |
| I | + | + | + | + | + | − |
| J | + | + | + | − | − | − |
| K | + | + | + | + | − | − |
| Betamethasone 17-valerate | + | + | + | − | − | − |
| 10–22 hours |  |  |  |  |  |  |
| I | + | + | + | + | − | − |
| J | + | + | + | − | − | − |
| K | + | + | + | − | − | − |
| Betamethasone 17-valerate | + | + | + | − | − | − |
| 24 Hours |  |  |  |  |  |  |
| I | + | + | + | + | − | − |
| J | + | + | + | − | − | − |
| K | + | + | + | − | − | − |
| Betamethasone 17-valerate | + | + | − | − | − | − |

In TABLE XIV above, "−" means a negative result was obtained. In other tables herein, "−" means not tested.

Human vasoconstriction testing has been used as an index of percutaneous absorption, activity and bioavailability of glucocorticoids. Compounds of the invention, structurally related compounds and well-known anti-inflammatory agents were compared. The results set forth in TABLE XII above show that, at 3 hours and 20 hours after removal of the patch, representative compounds of the invention of formula (I) showed vasoconstriction activity equal to or greater than betamethasone 17-valerate.

One hour re-occlusion at 20 hours after patch removal resulted in a distinct reappearance of pallor on the skin. Again, as shown in TABLE XIII above, representative compounds of the invention of formula (I) showed vasoconstriction activity equal to or greater than betamethasone 17-valerate.

In TABLE XIV above, the results of a simpler method of judging vasoconstriction activity was used in which only "positive" (pallor could be observed) or "negative" (pallor could not be detected) results were recorded. Once again, representative compounds of the invention of formula (I) showed equal or better activity than betamethasone 17-valerate.

TABLES XII, XIII and XIV also show that when the characteristic 17α-dichloroacetoxy group in the compounds of formula (I) is replaced with a 17α-chloroacetoxy, a 17α-(a-chloro)propionyloxy or a 17α-propionyloxy group, the local anti-inflammatory activity is greatly diminished. These tables also show that the instant 17α-dichloroacetoxy compounds generally display greatest activity when the 17β-group is an ethyl or methyl ester.

The compounds of formula (I) can be combined with suitable non-toxic pharmaceutically acceptable carriers to provide pharmaceutical compositions for use in the treatment of topical or other localized inflammation. Obviously, in view of their lack of systemic activity, the compounds of the present invention are not intended for treatment of conditions where systemic adrenocortical therapy is indicated, e.g., adrenocortical insufficiency. As examples of inflammatory conditions which can be treated with pharmaceutical compositions containing at least one compound of the invention and one or more pharmaceutical carriers, the following can be mentioned: dermatological disorders such as atopic dermatitis, acne, psoriasis or contact dermatitis; allergic states such as bronchial asthma; ophthalmic and otic diseases involving acute and chronic allergic and inflammatory reactions (for example, ophthalmic inflammatory conditions such as blepharitis, conjunctivitis, episcleritis, scleritis, keratitis, anterior uveitis and sympathetic ophthalmia); respiratory diseases; inflammations of the mouth, gums and/or throat, such as gingivitis or oral aphtha; inflammations of the nasal mucosa, for example, those caused by allergies; inflammations of the upper and lower intestines, such as ulcerative colitis; inflammations associated with arthritis; and anorectal inflammation, pruritus and pain associated with hemorrhoids, proctitis, cryptitis, fissures, postoperative pain and pruritus ani. Such compositions may also be applied locally as a prophylactic measure against the inflammation and tissue rejection which arise in connection with transplants.

Obviously, the choice of carrier(s) and dosage forms will vary with the particular condition for which the composition is to be administered.

Examples of various types of preparations for topical/local administration include ointments, lotions, creams, powders, drops (e.g., eye or ear or nose drops), sprays (e.g., for the nose or throat), suppositories, retention enemas, chewable or suckable tablets or pellets (e.g., for the treatment of aphthous ulcers) and aerosols. Ointments and creams may, for example, be formulated with an aqueous or oily base with the addition of suitable thickening and/or gelling agents and/or glycols. Such base may thus, for example, include water and/or an oil such as liquid paraffin or a vegetable oil such as arachis oil or castor oil, or a glycolic solvent such as propylene glycol or 1,3-butanediol. Thickening agents which may be used according to the nature of the base include soft paraffin, aluminum stearate, cetostearyl alcohol, polyethylene glycols, woolfat, hydrogenated lanolin and beeswax and/or glyceryl monostearate and/or non-ionic emulsifying agents.

The solubility of the steroid in the ointment or cream may be enhanced by incorporation of an aromatic alcohol such as benzyl alcohol, phenylethyl alcohol or phenoxyethyl alcohol.

Lotions may be formulated with an aqueous or oily base and will in general also include one or more of the following, namely, emulsifying agents, dispersing agents, suspending agents, thickening agents, solvents, coloring agents and perfumes. Powders may be formed with the aid of any suitable powder base e.g., talc, lactose or starch. Drops may be formulated with an aqueous base also comprising one or more dispersing agents, suspending agents or solubilizing agents, etc. Spray compositions may, for example, be formulated as aerosols with the use of a suitable propellant, e.g., dichlorodifluoromethane or trichlorofluoromethane.

Nebulized or powdered formulations may be prepared for oral inhalation in the treatment of asthma, as is well-known in the art. Solutions and suspensions may be prepared for oral or rectal administration for use in the treatment of inflammations of the intestines, for example, as described in more detail in the examples hereinafter. Parenteral/injectable formulations may be prepared for direct injection into the joints in the treatment of arthritis in accord with methods well-known to those skilled in the art of parenteral formulations.

The proportion of active ingredient in the compositions according to the invention will vary with the precise compound used, the type of formulation prepared and the particular condition for which the composition is to be administered. The formulation will generally contain from about 0.0001 to about 5.0% by weight of the compound of formula (I). Topical preparations will generally contain 0.0001 to 2.5%, preferably 0.01 to 0.5%, and will be administered once daily, or as needed. Also, generally speaking, the compounds of the invention can be incorporated into topical and other local compositions formulated substantially as are such presently available types of compositions containing known glucocorticosteroids, at approximately the same (or in the case of the most potent compounds of the invention, at proportionately lower) dosage levels as compared to known highly active agents such as methyl prednisolone acetate and beclomethasone dipropionate or at considerably lower dosage levels as compared to less active known agents such as hydrocortisone.

Thus, for example, an inhalation formulation suitable for use in the treatment of asthma can be prepared as a metered-dose aerosol unit containing a representative species of the invention such as ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate, according to procedures well-known to those skilled in the art of pharmaceutical formulations. Such an aerosol unit may contain a microcrystalline suspension of the aforementioned compound in suitable propellants (e.g., trichlorofluoromethane and dichlorodifluoromethane), with oleic acid or other suitable dispersing agent. Each unit typically contains 1–10 milligrams of the aforesaid active ingredient, approximately 5–50 micrograms of which are released at each actuation.

Another example of a pharmaceutical composition according to the invention is a foam suitable for treatment of a wide variety of inflammatory anorectal disorders, to be applied anally or perianally, comprising 0.05% to 0.1% of a compound of formula (I) such as ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate, and 1% of a local anaesthetic such as pramoxine hydrochloride, in a mucoadhesive foam base of propylene glycol, ethoxylated stearyl alcohol, polyoxyethylene-10-stearyl ether, cetyl alcohol, methyl paraben, propyl paraben, triethanolamine, and water, with inert propellants.

Yet another pharmaceutical formulation according to the invention is a solution or suspension suitable for use as a retention enema, a single dose of which typically contains 20–40 milligrams of a compound of the invention such as ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate, together with sodium chloride, polysorbate 80 and from 1 to 6 ounces of water (the water being added shortly before use). The suspension can be administered as a retention enema or by continuous drip several times weekly in the treatment of ulcerative colitis.

Other pharmaceutical formulations according to the invention are illustrated in the examples which follow.

Without further elaboration, it is believed that one of ordinary skill in the art can, using the preceding description, utilize the present invention to its fullest extent. Therefore, the following examples are to be construed as merely illustrative and not limitative of the remainder of the specification and claims in any way whatsoever.

In the synthetic examples which follow, all non-steroidal chemicals and solvents used were of reagent grade. All melting points were determined using a Fisher-Johns melting point apparatus and are uncorrected. The 300 MHz $^1$H-NMR data were obtained using a Varian T-90, QE-300 or Varian Unity-300 spectrometer and are reported in parts per million (δ) relative to tetramethylsilane. Elemental analyses were carried out by Atlantic Microlab, Inc., Atlanta, Ga. US. Mass spectra were obtained using a Kratos MFC 500 instrument and Fast Atom Bombardment (FAB). Thin-layer chromatography (TLC) was carried out using Merck DC-aluminum foil plates coated to a thickness of 0.2 mm with silica gel 60 containing fluorescent (254) indicator. Silica gel (particle size 32–63) was purchased from Selecto Scientific.

EXAMPLE 1

To a solution of prednisolone (15 g, 0.04 mol) in tetrahydrofuran (120 mL) and methanol (30 mL) at room temperature is added a warm (approximately 50° C.) solution of sodium metaperiodate (25.7 g, 0.12 mol) in water (100 mL). The reaction mixture is stirred at room temperature for 5 hours, then is concentrated under reduced pressure to remove tetrahydrofuran and methanol. The solid is triturated with 50 mL of water, separated by filtration, washed with water several times and dried in vacuo at 50° C. for 3 hours. The product, 11β,17α-dihydroxyandrosta-1,4-dien-3-one-17β-carboxylic acid 1 (which can also be termed $\Delta^1$-cortienic acid), is obtained as a white powder in approximately 94% yield (13.5 g), having a melting point of 231–232° C. $^1$H-NMR(DMSO-d$_6$) δ (ppm): 5.51 (s, 1, CH=CH), 1.41 (s, 3, 19-CH$_3$), 0.92 (s, 18-CH$_3$). Elemental analysis: Calculated for C$_{20}$H$_{26}$O$_5$: C, 69.36; H, 7.51. Found: C, 69.31; H, 7.56. The product has the structural formula:

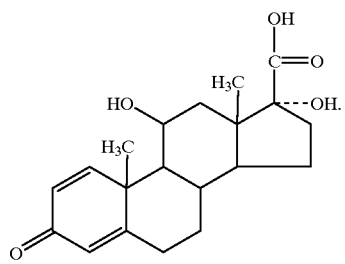

EXAMPLE 2

Substitution of an equivalent quantity of one of the starting materials listed in EXAMPLE 1 and substantial repetition of the procedure there detailed affords the indicated products:

| STARTING MATERIAL | PRODUCT |
|---|---|
| fludrocortisone | 9α-fluoro-11β, 17α-dihydroxyandrost-4-en-3-one-17β-carboxylic acid, m.p. 250–253° C. |
| betamethasone | 9α-fluoro-11β, 17α-dihydroxy-16β-methylandrosta-1,4-dien-3-one-17β-carboxylic acid, m.p. 248–249° C. |
| dexamethasone | 9α-fluoro-11β, 17α-dihydroxy-16α-methylandrosta-1,4-dien-3-one-17β-carboxylic acid, m.p. 275–278.5° C. |
| hydrocortisone | 11β, 17α-dihydroxyandrost-4-en-3-one-17β-carboxylic acid, m.p. 231–234° C. (i.e., cortienic acid) |

EXAMPLE 3

Substitution of an equivalent quantity of one of the starting materials listed below for the prednisolone used in EXAMPLE 1 and substantial repetition of the procedure there detailed affords the indicated products:

| STARTING MATERIAL | PRODUCT |
|---|---|
| cortisone | 17α-hydroxyandrost-4-en-3,11-dione-17β-carboxylic acid |
| chloroprednisone | 6a-chloro-17α-hydroxyandrosta-1,4-diene-3,11-dione-17β-carboxylic acid |
| flumethasone | 6α,9α-difluoro-11β,17α-dihydroxy-16α-methylandrosta-1,4-dien-3-one-17β-carboxylic acid |
| fluprednisolone | 6α-fluoro-11β,17α-dihydroxyandrosta-1,4-dien-3-one-17β-carboxylic acid |
| meprednisone | 17α-hydroxy-16β-methylandrosta-1,4-diene-3,11-dione-17β-carboxylic acid |
| methyl prednisolone | 11β,17α-dihydroxy-6α-methylandrosta-1,4-dien-3-one-17β-carboxylic acid |
| paramethasone | 6α-fluoro-11β,17α-dihydroxy-16α-methylandrosta-1,4-dien-3-one-17β-carboxylic acid |
| prednisone | 17α-hydroxyandrosta-1,4-diene-3,11-dione-17β-carboxylic acid |
| triamcinolone | 9α-fluoro-11β,16α,17α-trihydroxyandrosta-1,4-dien-3-one-17β-carboxylic acid |
| isofluprednone | 9α-fluoro-11β,17α-dihydroxyandrosta-1,4-dien-3-one-17β-carboxylic acid |
| 6α,9α-difluoroprednisolone | 6α,9α-difluoro-11β,17α-dihydroxyandrosta-1,4 dien-3-one-17β-carboxylic acid |
| beclomethasone | 9α-chloro-11β,17α-dihydroxy-16β-methylandrosta-1,4-dien-3-one-17β-carboxylic acid |
| 9α-chloro-6α-fluoro-16α-methylprednisolone | 9α-chloro-6α-fluoro-11β,17α-dihydroxy-16α-methylandrosta-1,4-dien-3-one-17β-carboxylic acid |
| 9α-fluoro-6α-methylprednisolone | 9α-fluoro-11β,17α-dihydroxy-6α-methylandrosta methylandrosta-1,4-dien-3-one-17β-carboxylic acid |
| dichlorisone | 9α,11β-dichloro-17α-hydroxyandrosta-1,4-dien-3-one-17β-carboxylic acid |
| 9a-chloro-16α-methylprednisolone | 9α-chloro-11β,17α-dihydroxy-16α-methylandrosta-1,4-dien-3-one-17β-carboxylic acid |

EXAMPLE 4

11β,17α-Dihydroxyandrosta-1,4-dien-3-one-17β-carboxylic acid 1 (3.12 g, 9.0 mmol) is dissolved in a solution of sodium bicarbonate (7.56 g, 90 mmol) in water (100 mL). Methylene chloride (100 mL) is added, followed by tetrabutylammonium hydrogensulfate (1.0 g). The mixture is stirred vigorously and dichloroacetyl chloride (1.51 g, 17 mmol) in methylene chloride (10 mL) is added dropwise over a period of 5 minutes. Stirring is continued for approximately 5 hours, then the organic phase is separated and washed successively with 5% aqueous sodium bicarbonate solution, water, and saturated aqueous sodium thiosulfate solution. The organic solution is dried over sodium sulfate and concentrated in vacuo. The resulting crude solid product is purified by chromatography, eluting with 1:100 by volume methanol: methylene chloride. $^1$H-NMR (DMSO-$d_6$) δ (ppm): 1.00 (s, 18-$CH_3$), 1.42 (s, 19-$CH_3$); 4.30 (m, 11-CH); 5.93 (s, 4-CH); 6.24 (m, 2-CH); 6.87 (s, $COCHCl_2$); 7.30 (m, 1-CH=C). FAB mass spectrum: 457 ($M^+$). Elemental analysis: Calculated for $C_{22}H_{26}O_6Cl_2$: C, 57.77; H, 5.69; Cl, 15.54. Found: C, 56.58; H, 5.83; Cl, 15.14. The product, 17α-dichloroacetoxy-11β-hydroxyandrosta-1,4-dien-3-one-17β-carboxylic acid 4, has the structural formula:

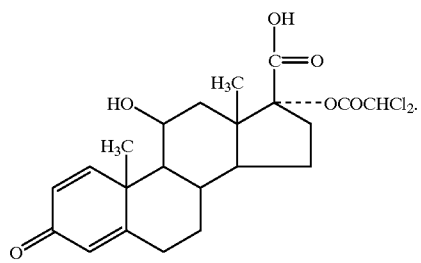

EXAMPLE 5

Substitution of an equivalent quantity of 9α-fluoro-11β,17α-dihydroxy-16α-methylandrosta-1,4-dien-3-one-17β-carboxylic acid for the 11β,17α-dihydroxyandrosta-1,4-dien-3-one-17β-carboxylic acid used in EXAMPLE 4 and substantial repetition of the procedure there detailed affords 17α-dichloroacetoxy-9α-fluoro-11β-hydroxy-16α-methylandrosta-1,4-dien-3-one-17β-carboxylic acid 5, which has the structural formula:

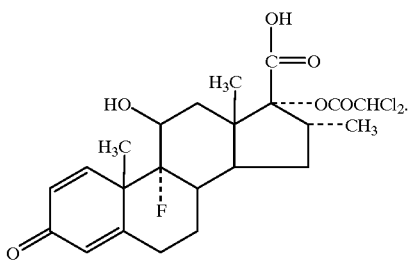

Purification of the crude product by flash chromatography on silica gel with 10:100 methanol:methylenechloride afforded 5 in 90% yield. MS: 490.7 ([M+H]), 510.7 ([M+Na]).

EXAMPLE 6

Following the general procedure of EXAMPLE 4 and substituting therein the appropriate reactants affords the following novel intermediates of the present invention:

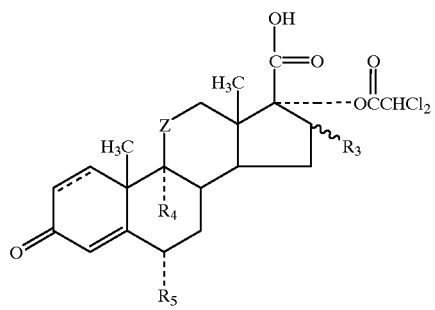

| Compound No. | $R_3$ | $R_4$ | $R_5$ | Z | Δ |
|---|---|---|---|---|---|
| 6-1 | H | H | H | \C(OH)(H) | 4 |
| 6-2 | H | F | H | \C(OH)(H) | 4 |
| 6-3 | β-$CH_3$ | F | H | \C(OH)(H) | 1, 4 |
| 6-4 | α-$CH_3$ | F | F | \C(OH)(H) | 1, 4 |

Compounds 6-1 to 6-4 above can be named as follows:
6-1: 17α-dichloroacetoxy-11β-hydroxyandrost-4-en-3-one-17β-carboxylic acid
6-2: 17α-dichloroacetoxy-9α-fluoro-11β-hydroxyandrost-4-en-3-one-17β-carboxylic acid
6-3: 17α-dichloroacetoxy-9α-fluoro-11β-hydroxy-16β-methylandrosta-1,4-dien-3-one-17β-carboxylic acid
6-4: 17α-dichloroacetoxy-6α,9α-difluoro-11β-hydroxy-16α-methylandrosta-1,4-dien-3-one-17β-carboxylic acid

EXAMPLE 7

Following the general procedure of EXAMPLE 4 and substituting therein the appropriate reactants affords the following novel intermediates of the present invention:

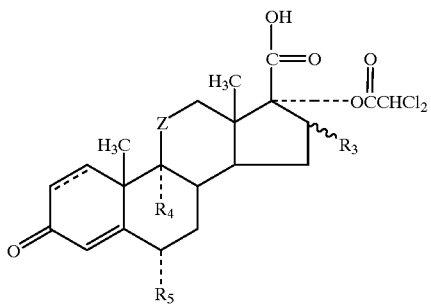
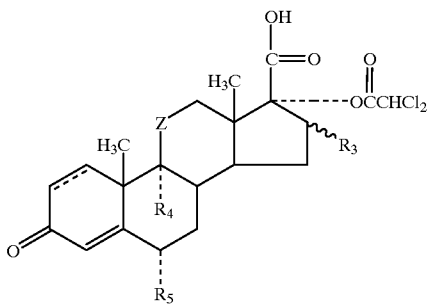

| Compound No. | $R_3$ | $R_4$ | $R_5$ | Z | Δ |
|---|---|---|---|---|---|
| 7-1 | H | H | H | >C=O | 4 |
| 7-2 | H | H | F | >C(OH)H | 1, 4 |
| 7-3 | β-CH₃ | H | H | >C=O | 1, 4 |
| 7-4 | α-CH₃ | H | F | >C(OH)H | 1, 4 |
| 7-5 | H | H | H | >C=O | 1, 4 |
| 7-6 | α-OCOCHCl₂ | F | H | >C(OH)H | 1, 4 |
| 7-7 | H | H | Cl | >C=O | 1, 4 |
| 7-8 | H | H | CH₃ | >C(OH)H | 1, 4 |
| 7-9 | H | F | H | >C(OH)H | 1, 4 |
| 7-10 | H | F | F | >C(OH)H | 1, 4 |
| 7-11 | β-CH₃ | Cl | H | >C(OH)H | 1, 4 |
| 7-12 | α-CH₃ | Cl | F | >C(OH)H | 1, 4 |
| 7-13 | H | F | CH₃ | >C(OH)H | 1, 4 |
| 7-14 | H | Cl | H | >C(Cl)H | 1, 4 |
| 7-15 | α-CH₃ | Cl | H | >C(OH)H | 1, 4 |

Compounds 7-1 to 7-15 can be named as follows:
7-1: 17α-dichloroacetoxyandrost-4-ene-3,11-dione-17β-carboxylic acid
7-2: 17α-dichloroacetory-6α-fluoro-11β-hydroxyandrosta-1,4-dien-3-one-17β-carboxylic acid
α7-3: 17α-dichloroacetoxy-16β-methylandrosta-1,4-diene-3,11-dione-17β-carboxylic acid
7-4: 17α-dichloroacetoxy-6α-fluoro-11β-hydroxy-16α-methylandrosta-1,4-dien-3-one-17β-carboxylic acid
7-5: 17α-dichloroacetoxyandrosta-1,4-diene-3,11-dione-17β-carboxylic acid
7-6: 16α,17α-bis(dichloroacetoxy)-9α-fluoro-11β-hydroxyandrosta-1,4-dien-3-one-17β-carboxylic acid
7-7: 6α-chloro-17α-dichloroacetoxyandrosta-1,4-diene-3,11-dione-17β-carboxylic acid
7-8: 17α-dichloroacetoxy-11β-hydroxy-6α-methylandrosta-1,4-dien-3-one-17β-carboxylic acid
7-9: 17α-dichloroacetoxy-9α-fluoro-11β-hydroxyandrosta-1,4-dien-3-one-17β-carboxylic acid
7-10: 17α-dichloroacetoxy-6α,9α-difluoro-11β-hydroxyandrosta-1,4-dien-3-one-17β-carboxylic acid
7-11: 9α-chloro-17α-dichloroacetoxy-11β-hydroxy-16β-methylandrosta-1,4-dien-3-one-17β-carboxylic acid
7-12: 9α-chloro-17α-dichloroacetoxy-6α-fluoro-11β-hydroxy-16α-methylandrosta-1,4-dien-3-one-17β-carboxylic acid
7-13: 17α-dichloroacetoxy-9α-fluoro-11β-hydroxy-6α-methylandrosta-1,4-dien-3-one-17β-carboxylic acid
7-14: 9α,11β-dichloro-17α-dichloroacetoxyandrosta-1,4-dien-3-one-17β-carboxylic acid
7-15: 9α-chloro-17α-dichloroacetoxy-11β-hydroxy-16α-methylandrosta-1,4-dien-3-one-17β-carboxylic acid

EXAMPLE 8

17α-Dichloroacetoxy-11β-hydroxyandrosta-1,4-dien-3-one-17β-carboxylic acid 4 (0.23 g, 0.5 mmol) is dissolved in a solution of sodium bicarbonate (0.2 g, 2.34 mmol) in water (50 mL). Methylene chloride (50 mL) is added, followed by tetrabutylammonium hydrogensulfate (0.2 g). The mixture is stirred vigorously while methyl iodide (0.16 g, 1.12 mmol) in methylene chloride (1 mL) is added dropwise over a period of 5 minutes. Stirring is continued for approximately 5 hours, then the organic phase is separated and washed successively with 5% aqueous sodium bicarbonate solution, water and saturated aqueous sodium thiosulfate solution. The organic solution is dried over sodium sulfate and concentrated in vacuo. The resulting crude solid product is purified by chromatography, eluting with 1:200 by volume methanol: methylene chloride. The product is obtained in 85% yield (0.2 g). Further purification by recrystallization from a mixture of n-hexane and diethyl ether affords methyl 17α-dichloroacetoxy-11β-hydroxyandrosta-1,4-dien-3-one-17β-carboxylate 8, melting at 115–117° C. and having the structural formula:

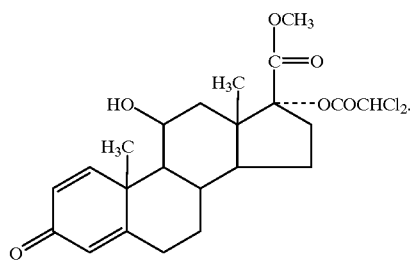

$^1$H-NMR (CDCl$_3$) δ (ppm): 1.02 (s, 18-CH$_3$); 1.40 (s, 19-CH$_3$); 3.75 (s, COOCH$_3$); 4.51 (m, 11-CH); 5.93 (s, 4-CH); 6.24 (m, 2-CH); 6.85 (s, COCHCl$_2$); 7.30 (m, 1-CH=C). FAB mass spectrum: 471 (M$^+$). Elemental analysis: Calculated for C$_{23}$H$_{28}$O$_6$Cl$_2$: C, 58.60; H, 5.94; Cl, 15.07. Found: C, 58.64; H, 6.15; Cl, 14.73.

EXAMPLE 9

Repetition of the general procedure of EXAMPLE 8, but using an equivalent quantity of ethyl iodide in place of the methyl iodide there employed, affords ethyl 17α-dichloroacetoxy-11β-hydroxyandrosta-1,4-dien-3-one-17β-carboxylate 9, melting at 208–210° C. and having the structural formula

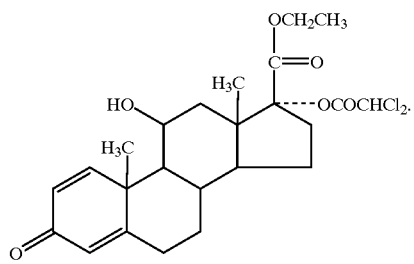

$^1$H-NMR (CDCl$_3$) δ (ppm): 1.05 (s, 18-CH$_3$); 1.27 (t, CH$_2$CH$_3$); 1.37 (s, 19-CH$_3$); 4.25 (s, COOCH$_2$); 4.51 (m, 11-CH); 5.93 (s, 4-CH); 6.24 (m, 2-CH); 6.87 (s, COCHCl$_2$); 7.30 (m, 1-CH=C). FAB mass spectrum: 485 (M$^+$). Elemental analysis: Calculated for C$_{24}$H$_{30}$O$_6$Cl$_2$: C, 59.38; H, 6.19; Cl, 14.64. Found: C, 59.48; H, 6.26; Cl, 14.72.

EXAMPLE 10

Repetition of the general procedure of EXAMPLE 8, but using an equivalent quantity of isopropyl iodide in place of the methyl iodide there employed affords isopropyl 17α-dichloroacetoxy-11β-hydroxyandrosta-1,4-dien-3-one-17β-carboxylate 10, melting at 222–223° C. and having the structural formula:

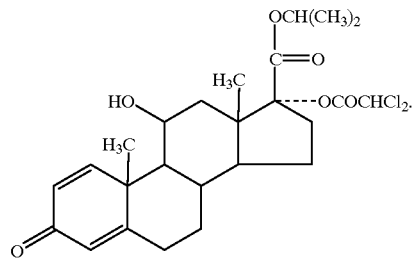

$^1$H-NMR (CDCl$_3$) δ (ppm): 1.01 (s, 18-CH$_3$); 1.22 (d, CH(CH$_3$)$_2$); 1.39 (s, 19-CH$_3$); 4.25 (s, COOCH); 4.51 (m, 11-CH); 5.93 (s, 4-CH); 6.24 (m, 2-CH); 6.86 (s, COCHCl$_2$); 7.32 (m, 1-CH=C). FAB mass spectrum: 499 (M$^+$). Elemental analysis: Calculated for C$_{25}$H$_{32}$O$_6$Cl$_2$: C, 60.12; H, 6.41; Cl, 14.23. Found: C, 59.99; H, 6.49; Cl, 14.31.

EXAMPLE 11

Repetition of the general procedure of EXAMPLE 8, but using an equivalent quantity of chloromethyl iodide in place of the methyl iodide there employed affords chloromethyl 17α-dichloroacetoxy-11β-hydroxyandrosta-1,4-dien-3-one-17β-carboxylate 11, melting at 122–123° C. and having the structural formula:

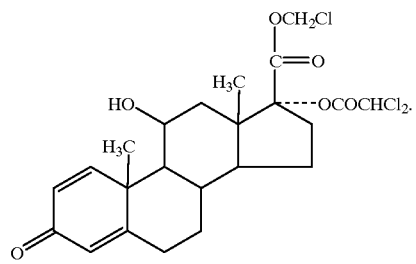

$^1$H-NMR (CDCl$_3$) δ (ppm): 0.98 (s, 18-CH$_3$); 1.36 (s, 19-CH$_3$); 4.45 (m, 11-C 5.76 (ABq, CH$_2$Cl); 5.95 (s, 4-CH); 6.24 (m, 2-CH); 6.89 (s, COCHCl$_2$); 7.28 (m, 1-CH=C). FAB mass spectrum: 505 (M$^+$). Elemental analysis: Calculated for C$_{23}$H$_{27}$O$_6$Cl$_3$: C, 54.65; H, 5.35; Cl, 21.09. Found: C, 54.61; H, 5.41; Cl, 20.94.

The same product is more preferably prepared by following the procedure described below:

17α-Dichloroacetoxy-11β-hydroxyandrosta-1,4-dien-3-one-17β-carboxylate 4 (0.024 mol) is dissolved in water (100 mL) containing sodium bicarbonate (9.90 g). Methylene chloride (80 mL) is added, followed by tetrabutylammonium hydrogensulfate (0.47 g, 1.18 mmol). Chloromethyl chlorosulfate (4.75 g, 0.029 mol) in methylene chloride (20 mL) is added dropwise over a period of 30 minutes while stirring vigorously. After stirring for 2 hours, the organic phase is separated, dried over sodium sulfate and evaporated to dryness in vacuo to give crude chloromethyl 17α-dichloroacetoxy-11β-hydroxyandrosta-1,4-dien-3-one-17β-carboxylate 11. After purification by chromatography and recrystallization as described in EXAMPLE 8, the product melts at 122–123° C.

EXAMPLE 12

Repetition of the general procedure of EXAMPLE 8, but using an equivalent quantity of 17α-dichloroacetoxy-9α- fluoro-11β-hydroxy-16α-methylandrosta-1,4-dien-3-one-17β-carboxylic acid 5 in place of the 17α-dichloroacetoxy-11β-hydroxyandrosta-1,4-dien-3-one-17β-carboxylic acid 2 there employed, affords methyl 17α-dichloroacetoxy-9α-fluoro-11β-hydroxy-16α-methylandrosta-1,4-dien-3-one-17β-carboxylate 12, having the structural formula:

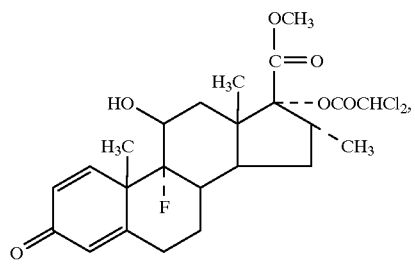

and being further characterized by a melting point of 248–251 °C.

EXAMPLE 13

Following the general procedure of EXAMPLE 8, and substituting therein the appropriate reactants affords the following compounds:

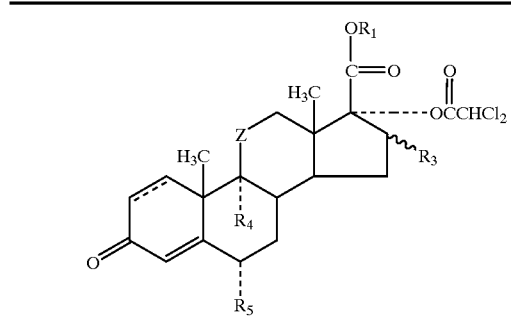

| Compound No. | $R_1$ | $R_3$ | $R_4$ | $R_5$ | Z | Δ |
|---|---|---|---|---|---|---|
| 13-1 | $C_2H_5$ | α-$CH_3$ | F | H | >C(OH)(H) | 1, 4 |
| 13-2 | iso-$C_3H_7$ | α-$CH_3$ | F | H | >C(OH)(H) | 1, 4 |
| 13-3 | $CH_2Cl$ | α-$CH_3$ | F | H | >C(OH)(H) | 1, 4 |
| 13-4 | $CH_3$ | H | H | H | >C(OH)(H) | 4 |

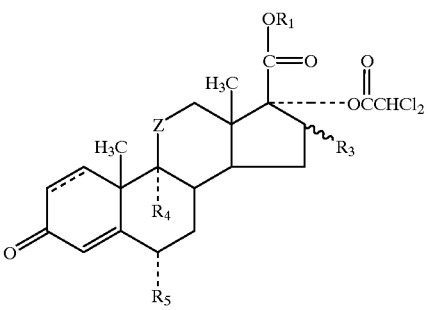

| Compound No. | $R_1$ | $R_3$ | $R_4$ | $R_5$ | Z | Δ |
|---|---|---|---|---|---|---|
| 13-5 | $C_2H_5$ | H | H | H | >C(OH)(H) | 4 |
| 13-6 | iso-$C_3H_7$ | H | H | H | >C(OH)(H) | 4 |
| 13-7 | $CH_2Cl$ | H | H | H | >C(OH)(H) | 4 |
| 13-8 | $CH_3$ | H | F | H | >C(OH)(H) | 4 |
| 13-9 | $C_2H_5$ | H | F | H | >C(OH)(H) | 4 |
| 13-10 | iso-$C_3H_7$ | H | F | H | >C(OH)(H) | 4 |
| 13-11 | $CH_2Cl$ | H | F | H | >C(OH)(H) | 4 |
| 13-12 | $CH_3$ | β-$CH_3$ | F | H | >C(OH)(H) | 1, 4 |
| 13-13 | $C_2H_5$ | β-$CH_3$ | F | H | >C(OH)(H) | 1, 4 |
| 13-14 | iso-$C_3H_7$ | β-$CH_3$ | F | H | >C(OH)(H) | 1, 4 |

| 39 | 40 |
|---|---|
| -continued | -continued |
| 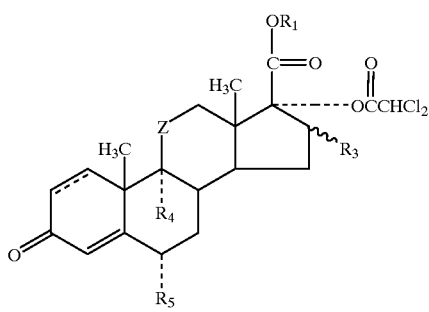 | 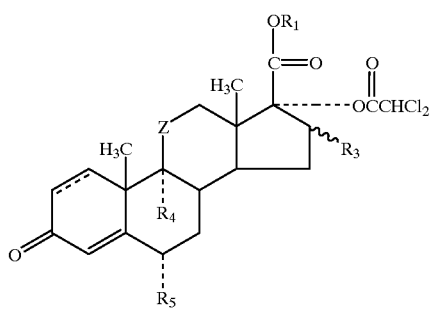 |

| Compound No. | R₁ | R₃ | R₄ | R₅ | Z | Δ | Compound No. | R₁ | R₃ | R₄ | R₅ | Z | Δ |
|---|---|---|---|---|---|---|---|---|---|---|---|---|---|
| 13-15 | CH₂Cl | β-CH₃ | F | H | >C(OH)(H) | 1, 4 | 13-25 | C₂H₅ | H | H | F | >C(OH)(H) | 1, 4 |
| 13-16 | CH₃ | α-CH₃ | F | F | >C(OH)(H) | 1, 4 | 13-26 | iso-C₃H₇ | H | H | F | >C(OH)(H) | 1, 4 |
| 13-17 | C₂H₅ | α-CH₃ | F | F | >C(OH)(H) | 1, 4 | 13-27 | CH₂Cl | H | H | F | >C(OH)(H) | 1, 4 |
| 13-18 | iso-C₃H₇ | α-CH₃ | F | F | >C(OH)(H) | 1, 4 | 13-28 | CH₃ | β-CH₃ | H | H | >C=O | 1, 4 |
| 13-19 | CH₂Cl | α-CH₃ | F | F | >C(OH)(H) | 1, 4 | 13-29 | C₂H₅ | β-CH₃ | H | H | >C=O | 1, 4 |
| 13-20 | CH₃ | H | H | H | >C=O | 4 | 13-30 | iso-C₃H₇ | β-CH₃ | H | H | >C=O | 1, 4 |
| 13-21 | C₂H₅ | H | H | H | >C=O | 4 | 13-31 | CH₂Cl | β-CH₃ | H | H | >C=O | 1, 4 |
| 13-22 | iso-C₃H₇ | H | H | H | >C=O | 4 | 13-32 | CH₃ | α-CH₃ | H | F | >C(OH)(H) | 1, 4 |
| 13-23 | CH₂Cl | H | H | H | >C=O | 4 | 13-33 | C₂H₅ | α-CH₃ | H | F | >C(OH)(H) | 1, 4 |
| 13-24 | CH₃ | H | H | F | >C(OH)(H) | 1, 4 | 13-34 | iso-C₃H₇ | α-CH₃ | H | F | >C(OH)(H) | 1, 4 |

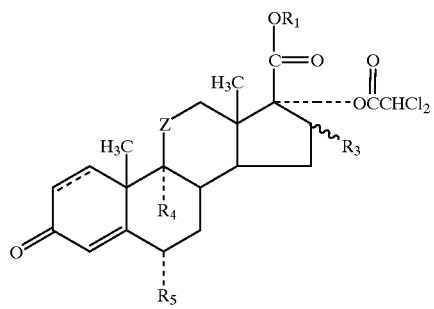
| Compound No. | $R_1$ | $R_3$ | $R_4$ | $R_5$ | Z | Δ |
|---|---|---|---|---|---|---|
| 13-35 | $CH_2Cl$ | α-$CH_3$ | H | F |  | 1, 4 |
| 13-36 | $CH_3$ | H | H | H |  | 1, 4 |
| 13-37 | $C_2H_5$ | H | H | H |  | 1, 4 |
| 13-38 | iso-$C_3H_7$ | H | H | H |  | 1, 4 |
| 13-39 | $CH_2Cl$ | H | H | H |  | 1, 4 |
| 13-40 | $CH_3$ | α-$OCOCHCl_2$ | F | H |  | 1, 4 |
| 13-41 | $C_2H_5$ | α-$OCOCHCl_2$ | F | H | | 1, 4 |
| 13-42 | iso-$C_3H_7$ | α-$OCOCHCl_2$ | F | H | | 1, 4 |
| 13-43 | $CH_2Cl$ | α-$OCOCHCl_2$ | F | H | | 1, 4 |
| 13-44 | $CH_3$ | H | H | Cl | | 1, 4 |
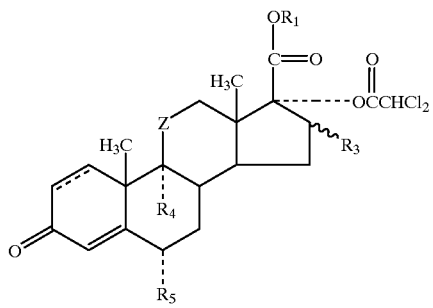
| Compound No. | $R_1$ | $R_3$ | $R_4$ | $R_5$ | Z | Δ |
|---|---|---|---|---|---|---|
| 13-45 | $C_2H_5$ | H | H | Cl |  | 1, 4 |
| 13-46 | iso-$C_3H_7$ | H | H | Cl |  | 1, 4 |
| 13-47 | $CH_2Cl$ | H | H | Cl |  | 1, 4 |
| 13-48 | $CH_3$ | H | H | $CH_3$ |  | 1, 4 |
| 13-49 | $C_2H_5$ | H | H | $CH_3$ |  | 1, 4 |
| 13-50 | iso-$C_3H_7$ | H | H | $CH_3$ | | 1, 4 |
| 13-51 | $CH_2Cl$ | H | H | $CH_3$ |  | 1, 4 |
| 13-52 | $CH_3$ | H | F | H | | 1, 4 |
| 13-53 | $C_2H_5$ | H | F | H |  | 1, 4 |
| 13-54 | iso-$C_3H_7$ | H | F | H | | 1, 4 |

-continued

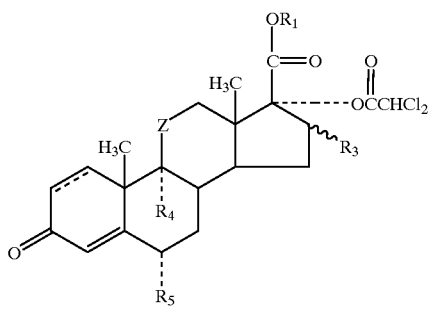

| Compound No. | $R_1$ | $R_3$ | $R_4$ | $R_5$ | Z | Δ |
|---|---|---|---|---|---|---|
| 13-55 | $CH_2Cl$ | H | F | H | >C(OH)(H)- | 1, 4 |
| 13-56 | $CH_3$ | H | F | F | >C(OH)(H)- | 1, 4 |
| 13-57 | $C_2H_5$ | H | F | F | >C(OH)(H)- | 1, 4 |
| 13-58 | iso-$C_3H_7$ | H | F | F | >C(OH)(H)- | 1, 4 |
| 13-59 | $CH_2Cl$ | H | F | F | >C(OH)(H)- | 1, 4 |
| 13-60 | $CH_3$ | β-$CH_3$ | Cl | H | >C(OH)(H)- | 1, 4 |
| 13-61 | $C_2H_5$ | β-$CH_3$ | Cl | H | >C(OH)(H)- | 1, 4 |
| 13-62 | iso-$C_3H_7$ | β-$CH_3$ | Cl | H | >C(OH)(H)- | 1, 4 |
| 13-63 | $CH_2Cl$ | β-$CH_3$ | Cl | H | >C(OH)(H)- | 1, 4 |
| 13-64 | $CH_3$ | α-$CH_3$ | Cl | F | >C(OH)(H)- | 1, 4 |

-continued

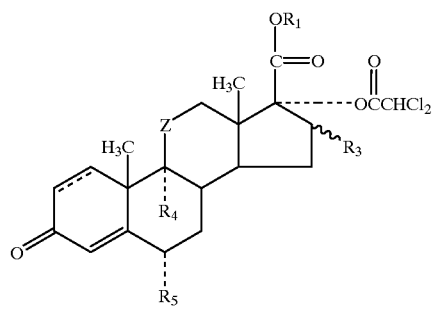

| Compound No. | $R_1$ | $R_3$ | $R_4$ | $R_5$ | Z | Δ |
|---|---|---|---|---|---|---|
| 13-65 | $C_2H_5$ | α-$CH_3$ | Cl | F | >C(OH)(H)- | 1, 4 |
| 13-66 | iso-$C_3H_7$ | α-$CH_3$ | Cl | F | >C(OH)(H)- | 1, 4 |
| 13-67 | $CH_2Cl$ | α-$CH_3$ | Cl | F | >C(OH)(H)- | 1, 4 |
| 13-68 | $CH_3$ | H | F | $CH_3$ | >C(OH)(H)- | 1, 4 |
| 13-69 | $C_2H_5$ | H | F | $CH_3$ | >C(OH)(H)- | 1, 4 |
| 13-70 | iso-$C_3H_7$ | H | F | $CH_3$ | >C(OH)(H)- | 1, 4 |
| 13-71 | $CH_2Cl$ | H | F | $CH_3$ | >C(OH)(H)- | 1, 4 |
| 13-72 | $CH_3$ | H | Cl | H | >C(Cl)(H)- | 1, 4 |
| 13-73 | $C_2H_5$ | H | Cl | H | >C(Cl)(H)- | 1, 4 |
| 13-74 | iso-$C_3H_7$ | H | Cl | H | >C(Cl)(H)- | 1, 4 |

-continued

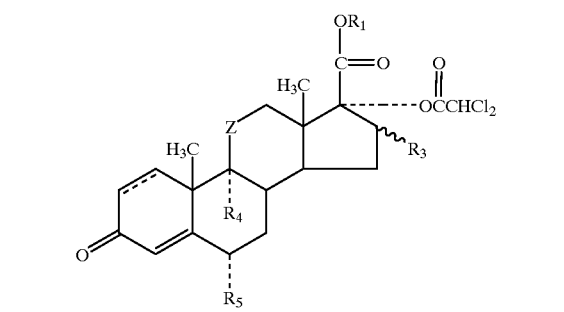

| Compound No. | $R_1$ | $R_3$ | $R_4$ | $R_5$ | Z | Δ |
|---|---|---|---|---|---|---|
| 13-75 | $CH_2Cl$ | H | Cl | H | 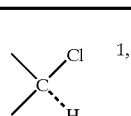 | 1, 4 |
| 13-76 | $CH_3$ | α-$CH_3$ | Cl | H | 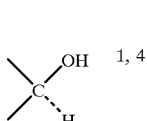 | 1, 4 |
| 13-77 | $C_2H_5$ | α-$CH_3$ | Cl | H | 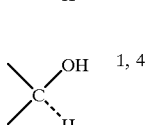 | 1, 4 |
| 13-78 | iso-$C_3H_7$ | α-$CH_3$ | Cl | H | 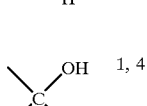 | 1, 4 |
| 13-79 | $CH_2Cl$ | α-$CH_3$ | Cl | H | 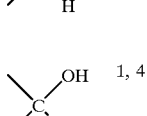 | 1, 4 |
| 13-80 | n-$C_3H_7$ | H | H | H | 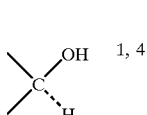 | 1, 4 |
| 13-81 | n-$C_4H_9$ | H | H | H | 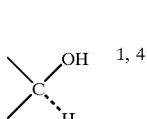 | 1, 4 |
| 13-82 | n-$C_3H_7$ | H | F | H | 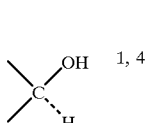 | 1, 4 |
| 13-83 | n-$C_4H_9$ | H | F | H | 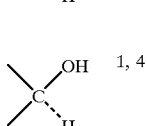 | 1, 4 |
| 13-84 | n-$C_3H_7$ | H | F | F | 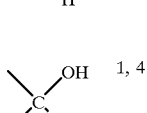 | 1, 4 |

-continued

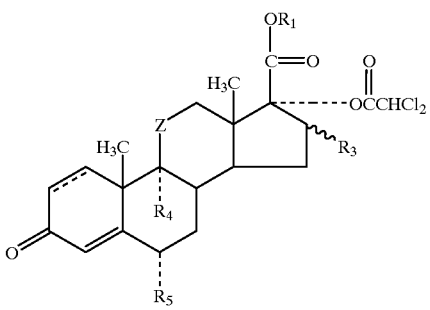

| Compound No. | $R_1$ | $R_3$ | $R_4$ | $R_5$ | Z | Δ |
|---|---|---|---|---|---|---|
| 13-85 | n-$C_4H_9$ | H | F | F | 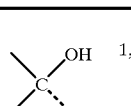 | 1, 4 |
| 13-86 | n-$C_3H_7$ | H | H | F | 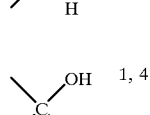 | 1, 4 |
| 13-87 | n-$C_4H_9$ | H | H | F | 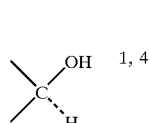 | 1, 4 |
| 13-88 | n-$C_3H_7$ | α-$OCOCHCl_2$ | F | H | 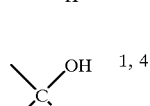 | 1, 4 |
| 13-89 | n-$C_4H_9$ | α-$OCOCHCl_2$ | F | H | 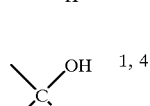 | 1, 4 |
| 13-90 | n-$C_3H_7$ | H | Cl | H | 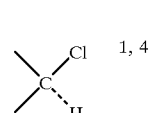 | 1, 4 |
| 13-91 | n-$C_4H_9$ | H | Cl | H | 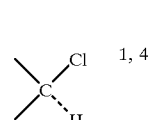 | 1, 4 |
| 13-92 | n-$C_3H_7$ | H | F | $CH_3$ | 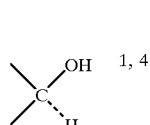 | 1, 4 |
| 13-93 | n-$C_4H_9$ | H | F | $CH_3$ | 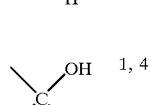 | 1, 4 |

The foregoing compounds can be named as follows:

13-1: ethyl 17α-dichloroacetoxy-9α-fluoro-11β-hydroxy-16α-methylandrosta-1,4-dien-3-one-17β-carboxylate 13-2: isopropyl 17α-dichloroacetoxy-9α-fluoro-11β-hydroxy-16α-methylandrosta-1,4-dien-3-one-17β-carboxylate 13-3: chloromethyl 17α-dichloroacetoxy-9α-fluoro-11β-hydroxy-16α-methylandrosta-1,4-dien-3-one-17β-carboxylate 13-4: methyl 17α-dichloroacetoxy-11β-hydroxyandrost-4-en-3-one-17β-carboxylate 13-5: ethyl 17α-dichloroacetoxy-11β-hydroxyandrost-4-en-3-one-17β-carboxylate 13-6: isopropyl 17α-dichloroacetoxy-11β-hydroxyandrost-4-en-3-one-17ε-carboxylate 13-7: chloromethyl 17α-dichloroacetoxy-11ε-hydroxyandrost-4-en-3-one-17β-carboxylate α13-8: methyl 17α-dichloroacetoxy-9α-fluoro-11β-hydroxyandrost-4-en-3-one-17ε-carboxylate α13-9: ethyl 17α-dichloroacetoxy-9α-fluoro-11β-hydroxyandrost-4-en-3-one-17β-carboxylate 13-10: isopropyl 17α-dichloroacetoxy-9α-fluoro-11β-hydroxyandrost-4-en-3-one-17β-carboxylate 13-11: chloromethyl 17α-dichloroacetoxy-9α-fluoro-11β-hydroxyandrost-4-en-3-one-17β-carboxylate 13-12: methyl 17α-dichloroacetoxy-9α-fluoro-11β-hydroxy-16β-methylandrosta-1,4-dien-3-one-17β-carboxylate 13-13: ethyl 17α-dichloroacetoxy-9α-fluoro-11β-hydroxy-16β-methylandrosta-1,4-dien-3-one-17β-carboxylate 13-14: isopropyl 17α-dichloroacetoxy-9α-fluoro-11β-hydroxy-16β-methylandrosta-1,4-dien-3-one-17β-carboxylate 13-15: chloromethyl 17α-dichloroacetoxy-9α-fluoro-11β-hydroxy-16β-methylandrosta-1,4-dien-3-one-17β-carboxylate 13-16: methyl 17α-dichloroacetoxy-6α,9α-difluoro-11β-hydroxy-16β-methylandrosta-1,4-dien-3-one-17β-carboxylate 13-17: ethyl 17α-dichloroacetoxy-6α,9α-difluoro-11β-hydroxy-16α-methylandrosta-1,4-dien-3-one-17β-carboxylate 13-18: isopropyl 17α-dichloroacetoxy-6α,9α-difluoro-11β-hydroxy-16α-methylandrosta-1,4-dien-3-one-17β-carboxylate 13-19: chloromethyl 17α-dichloroacetoxy-6α,9α-difluoro-11β-hydroxy-16α-methylandrosta-1,4-dien-3-one-17β-carboxylate 13-20: methyl 17α-dichloroacetoxyandrost-4-ene-3,11-dione-17β-carboxylate 13-21: ethyl 17α-dichloroacetoxyandrost-4-ene-3,11-dione-17β-carboxylate 13-22: isopropyl 17α-dichloroacetoxyandrost-4-ene-3,11-dione-17β-carboxylate 13-23: chloromethyl 17α-dichloroacetoxyandrost-4-ene-3,11-dione-17β-carboxylate 13-24: methyl 17α-dichloroacetoxy-6α-fluoro-11β-hydroxyandrosta-1,4-dien-3-one-17β-carboxylate 13-25: ethyl 17α-dichloroacetoxy-6α-fluoro-11β-hydroxyandrosta-1,4-dien-3-one-17β-carboxylate 13-26: isopropyl 17α-dichloroacetoxy-6α-fluoro-11β-hydroxyandrosta-1,4-dien-3-one-17β-carboxylate 13-27: chloromethyl 17α-dichloroacetoxy-6α-fluoro-11β-hydroxyandrosta-1,4-dien-3-one-17β-carboxylate 13-28: methyl 17α-dichloroacetoxy-16β-methylandrosta-1,4-diene-3,11-dione-17β-carboxylate 13-29: ethyl 17α-dichloroacetoxy-16β-methylandrosta-1,4-diene-3,11-dione-17β-carboxylate 13-30: isopropyl 17α-dichloroacetoxy-16β-methylandrosta-1,4-diene-3,11-dione-17β-carboxylate 13-31: chloromethyl 17α-dichloroacetoxy-16β-methylandrosta-1,4-diene-3,11-dione-17β-carboxylate 13-32: methyl 17α-dichloroacetoxy-6α-fluoro-11β-hydroxy-16α-methylandrosta-1,4-dien-3-one-17β-carboxylate 13-33: ethyl 17α-dichloroacetoxy-6α-fluoro-11β-hydroxy-16α-methylandrosta-1,4-dien-3-one-17β-carboxylate 13-34: isopropyl 17α-dichloroacetoxy-6α-fluoro-11β-hydroxy-16α-methylandrosta-1,4-dien-3-one-17β-carboxylate 13-35: chloromethyl 17α-dichloroacetoxy-6α-fluoro-11β-hydroxy-16α-methylandrosta-1,4-dien-3-one-17β-carboxylate 13-36: methyl 17α-dichloroacetoxyandrosta-1,4-diene-3,11-dione-17β-carboxylate 13-37: ethyl 17α-dichloroacetoxyandrosta-1,4-diene-3,11-dione-17β-carboxylate 13-38: isopropyl 17α-dichloroacetoxyandrosta-1,4-diene-3,11-dione-17ε-carboxylate 13-39: chloromethyl 17α-dichloroacetoxyandrosta-1,4-diene-3,11-dione-17β-carboxylate 13-40: methyl 16α,17α-bis(dichloroacetoxy)-9α-fluoro-11β-hydroxyandrosta-1,4-dien-3-one-17β-carboxylate 13-41: ethyl 16α,17α-bis(dichloroacetoxy)-9α-fluoro-11β-hydroxyandrosta-1,4-dien-3-one-17β-carboxylate 13-42: isopropyl 16α,17α-bis(dichloroacetoxy)-9α-fluoro-11β-hydroxyandrosta-1,4-dien-3-one-17β-carboxylate 13-43: chloromethyl 16α,17α-bis(dichloroacetoxy)-9α-fluoro-11β-hydroxyandrosta-1,4-dien-3-one-17β-carboxylate 13-44: methyl 6α-chloro-17α-dichloroacetoxyandrosta-1,4-diene-3,11-dione-17β-carboxylate 13-45: ethyl 6α-chloro-17α-dichloroacetoxyandrosta-1,4-diene-3,11-dione-17β-carboxylate 13-46: isopropyl 6α-chloro-17α-dichloroacetoxyandrosta-1,4-diene-3,11-dione-17β-carboxylate 13-47: chloromethyl 6α-chloro-17α-dichloroacetoxyandrosta-1,4-diene-3,11-dione-17β-carboxylate 13-48: methyl 17α-dichloroacetoxy-11β-hydroxy-6α-methylandrosta-1,4-dien-3-one-17β-carboxylate 13-49: ethyl 17α-dichloroacetoxy-11β-hydroxy-6α-methylandrosta-1,4-dien-3-one-17β-carboxylate 13-50: isopropyl 17α-dichloroacetoxy-11β-hydroxy-6α-methylandrosta-1,4-dien-3-one-17β-carboxylate 13-51: chloromethyl 17α-dichloroacetoxy-11β-hydroxy-6α-methylandrosta-1,4-dien-3-one-17β-carboxylate 13-52: methyl 17α-dichloroacetoxy-9α-fluoro-11β-hydroxyandrosta-1,4-dien-3-one-17β-carboxylate 13-53: ethyl 17α-dichloroacetoxy-9α-fluoro-11β-hydroxyandrosta-1,4-dien-3-one-17β-carboxylate 13-54: isopropyl 17α-dichloroacetoxy-9α-fluoro-11β-hydroxyandrosta-1,4-dien-3-one-17β-carboxylate 13-55: chloromethyl 17α-dichloroacetoxy-9α-fluoro-11β-hydroxyandrosta-1,4-dien-3-one-17β-carboxylate 13-56: methyl 17α-dichloroacetoxy-6α,9α-difluoro-11β-hydroxyandrosta-1,4-dien-3-one-17β-carboxylate 13-57: ethyl 17α-dichloroacetoxy-6α,9α-difluoro-11β-hydroxyandrosta-1,4-dien-3-one-17β-carboxylate 13-58: isopropyl 17α-dichloroacetoxy-6α,9α-difluoro-11β-hydroxyandrosta-1,4-dien-3-one-17β-carboxylate 13-59: chloromethyl 17α-dichloroacetoxy-6α,9α-difluoro-11β-hydroxyandrosta-1,4-dien-3-one-17β-carboxylate 13-60: methyl 9α-chloro-17α-dichloroacetoxy-11β-hydroxy-16β-methylandrosta-1,4-dien-3-one-17β-carboxylate 13-61: ethyl 9α-chloro-17α-dichloroacetoxy-11β-hydroxy-16β-methylandrosta-1,4-dien-3-one-17β-carboxylate 13-62: isopropyl 9α-chloro-17α-dichloroacetoxy-11β-hydroxy-16β-methylandrosta-1,4-dien-3-one-17β-carboxylate
13-63: chloromethyl 9α-chloro-17α-dichloroacetoxy-11β-hydroxy-16β-methylandrosta-1,4-dien-3-one-17β-carboxylate
13-64: methyl 9α-chloro-17α-dichloroacetoxy-6α-fluoro-11β-hydroxy-16α-methylandrosta-1,4-dien-3-one-17β-carboxylate
13-65: ethyl 9α-chloro-17α-dichloroacetoxy-6α-fluoro-11β-hydroxy-16α-methylandrosta-1,4-dien-3-one-17β-carboxylate
13-66: isopropyl 9α-chloro-17α-dichloroacetoxy-6α-fluoro-11β-hydroxy-16α-methylandrosta-1,4-dien-3-one-17β-carboxylate
13-67: chloromethyl 9α-chloro-17α-dichloroacetoxy-6α-fluoro-11β-hydroxy-16α-methylandrosta-1,4-dien-3-one-17β-carboxylate
13-68: methyl 17α-dichloroacetoxy-9α-fluoro-11β-hydroxy-6α-methylandrosta-1,4-dien-3-one-17β-carboxylate
13-69: ethyl 17α-dichloroacetoxy-9α-fluoro-11β-hydroxy-6α-methylandrosta-1,4-dien-3-one-17β-carboxylate
13-70: isopropyl 17α-dichloroacetoxy-9α-fluoro-11β-hydroxy-6α-methylandrosta-1,4-dien-3-one-17β-carboxylate
13-71: chloromethyl 17α-dichloroacetoxy-9α-fluoro-11β-hydroxy-6α-methylandrosta-1,4-dien-3-one-17β-carboxylate
13-72: methyl 9α,11β-dichloro-17α-dichloroacetoxyandrosta-1,4-dien-3-one-17β-carboxylate
13-73: ethyl 9α,11β-dichloro-17α-dichloroacetoxyandrosta-1,4-dien-3-one-17β-carboxylate
13-74: isopropyl 9α,11β-dichloro-17α-dichloroacetoxyandrosta-1,4-dien-3-one-17β-carboxylate
13-75: chloromethyl 9α,11β-dichloro-17α-dichloroacetoxyandrosta-1,4-dien-3-one-17β-carboxylate
13-76: methyl 9α-chloro-17α-dichloroacetoxy-11β-hydroxy-16α-methylandrosta-1,4-dien-3-one-17β-carboxylate
13-77: ethyl 9α-chloro-17α-dichloroacetoxy-11β-hydroxy-16α-methylandrosta-1,4-dien-3-one-17β-carboxylate
13-78: isopropyl 9α-chloro-17α-dichloroacetoxy-11β-hydroxy-16α-methylandrosta-1,4-dien-3-one-17β-carboxylate
13-79: chloromethyl 9α-chloro-17α-dichloroacetoxy-11β-hydroxy-16α-methylandrosta-1,4-dien-3-one-17β-carboxylate
13-80: n-propyl 17α-dichloroacetoxy-11β-hydroxyandrosta-1,4-dien-3-one-17β-carboxylate
13-81: n-butyl 17α-dichloroacetoxy-11β-hydroxyandrosta-1,4-dien-3-one-17β-carboxylate
13-82: n-propyl 17α-dichloroacetoxy-9α-fluoro-11β-hydroxyandrosta-1,4-dien-3-one-17β-carboxylate
13-83: n-butyl 17α-dichloroacetoxy-9α-fluoro-11β-hydroxyandrosta-1,4-dien-3-one-17β-carboxylate
13-84: n-propyl 17α-dichloroacetoxy-6α,9α-difluoro-11β-hydroxyandrosta-1,4-dien-3-one-17β-carboxylate
13-85: n-butyl 17α-dichloroacetoxy-6α,9α-difluoro-11β-hydroxyandrosta-1,4-dien-3-one-17β-carboxylate
13-86: n-propyl 17α-dichloroacetoxy-6α-fluoro-11β-hydroxyandrosta-1,4-dien-3-one-17β-carboxylate
13-87: n-butyl 17α-dichloroacetoxy-6α-fluoro-11β-hydroxyandrosta-1,4-dien-3-one-17β-carboxylate
13-88: n-propyl 16α,17α-bis(dichloroacetoxy)-9α-fluoro-11β-hydroxyandrosta-1,4-dien-3-one-17β-carboxylate
13-89: n-butyl 16α,17α-bis(dichloroacetoxy)-9α-fluoro-11β-hydroxyandrosta-1,4-dien-3-one-17β-carboxylate
13-90: n-propyl 9α,11β-dichloro-17α-dichloroacetoxyandrosta-1,4-dien-3-one-17β-carboxylate
13-91: n-butyl 9α,11β-dichloro-17α-dichloroacetoxyandrosta-1,4-dien-3-one-17β-carboxylate
13-92: n-propyl 17α-dichloroacetoxy-9α-fluoro-11β-hydroxy-6α-methylandrosta-1,4-dien-3-one-17β-carboxylate
13-93: n-butyl 17α-dichloroacetoxy-9α-fluoro-11β-hydroxy-6α-methylandrosta-1,4-dien-3-one-17β-carboxylate

EXAMPLE 14

The products of EXAMPLE 4 and EXAMPLE 5, Compounds 2 and 4, respectively, are each allowed to react, first with diethylchlorophosphate and then with $CH_3SNa$ in chloroform for approximately 6 hours. The following intermediates are obtained in the first step:

| Compound No. | $R_3$ | $R_4$ | Δ |
|---|---|---|---|
| 14-1 | H | H | 1, 4 |
| 14-2 | α-$CH_3$ | F | 1, 4 | and the following compounds of formula (I) are obtained in the second step:

| Compound No. | $R_3$ | $R_4$ | Δ |
|---|---|---|---|
| 14-3 | H | H | 1, 4 |
| 14-4 | α-$CH_3$ | F | 1, 4 |

When the products of EXAMPLE 6 and those of EXAMPLE 7 are treated according to the above two step procedure, the corresponding compounds of the formula:

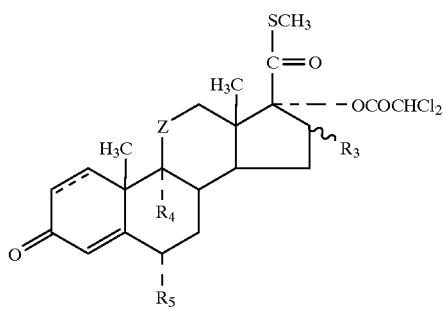

are obtained:

| Compound No. | Starting Material | R₃ | R₄ | R₅ | Z | Δ |
|---|---|---|---|---|---|---|
| 14-5 | 6-1 | H | H | H | >C(OH)(H) | 4 |
| 14-6 | 6-2 | H | F | H | >C(OH)(H) | 4 |
| 14-7 | 6-3 | β-CH₃ | F | H | >C(OH)(H) | 1, 4 |
| 14-8 | 6-4 | α-CH₃ | F | F | >C(OH)(H) | 1, 4 |
| 14-9 | 7-1 | H | H | H | >C=O | 4 |
| 14-10 | 7-2 | H | H | F | >C(OH)(H) | 1, 4 |
| 14-11 | 7-3 | β-CH₃ | H | H | >C=O | 1, 4 |
| 14-12 | 7-4 | α-CH₃ | H | F | >C(OH)(H) | 1, 4 |
| 14-13 | 7-5 | H | H | H | >C=O | 1, 4 |
| 14-14 | 7-6 | α-COCHCl₂ | F | H | >C(OH)(H) | 1, 4 |
| 14-15 | 7-7 | H | H | Cl | >C=O | 1, 4 |
| 14-16 | 7-8 | H | H | CH₃ | >C(OH)(H) | 1, 4 |
| 14-17 | 7-9 | H | F | H | >C(OH)(H) | 1, 4 |
| 14-18 | 7-10 | H | F | F | >C(OH)(H) | 1, 4 |
| 14-19 | 7-11 | β-CH₃ | Cl | H | >C(OH)(H) | 1, 4 |
| 14-20 | 7-12 | α-CH₃ | Cl | F | >C(OH)(H) | 1, 4 |
| 14-21 | 7-13 | H | F | CH₃ | >C(OH)(H) | 1, 4 |
| 14-22 | 7-14 | H | Cl | H | >C(Cl)(H) | 1, 4 |
| 14-23 | 7-15 | α-CH₃ | Cl | H | >C(OH)(H) | 1, 4 |

EXAMPLE 15

17α-Dichloroacetoxy-11β-hydroxyandrosta-1,4-dien-3-one-17β-carboxylic acid, 4 (7.00 mmol), is treated with 7.00 mL of 1M methanolic sodium hydroxide solution, and 500 mL of ethyl ether are then added to effect precipitation. The precipitate is separated by filtration and dried in an evacuated desiccator overnight to afford the desired salt, i.e., sodium 17α-dichloroacetoxy-11β-hydroxyandrosta-1,4-dien-3-one-17β-carboxylate. The salt is dissolved in 40 mL of hexamethylphosphoramide and 1 equivalent of chloromethyl methyl sulfide is added slowly. A precipitate of sodium chloride forms rapidly. The reaction mixture is stirred at room temperature for approximately 1 hour, then is diluted with ethyl acetate to a total volume of 200 mL and washed successively with 3% sodium bicarbonate and water. The organic layer is separated, dried with magnesium sulfate and filtered. The filtrate is concentrated in vacuo to an oil, and the oil is chromatographed from silica gel, using ethyl acetate, chloroform and acetic acid as eluants. The chromatographed product is crystallized from a mixture of ethyl ether and hexane to give methylthiomethyl 17α-dichloroacetoxy-11β-hydroxyandrosta-1,4-dien-3-one-17β-carboxylate, which is characterized by the structural formula

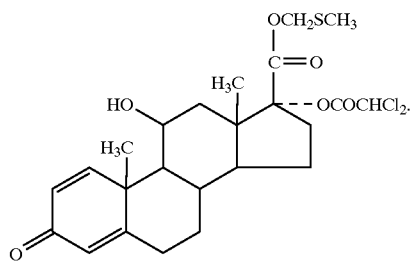

To a solution of methylthiomethyl 17α-dichloroacetoxy-11β-hydroxyandrosta-1,4-dien-3-one-17β-carboxylate (1 mmol) in 2 mL of dichloromethane is added m-chloroperoxybenzoic acid (2 mmol of peracid). An exothermic reaction ensues, which subsides quickly. The reaction mixture is stirred at room temperature for 1 hour. The precipitate which forms is removed by filtration and the filtrate is concentrated in vacuo to afford methylsufonylmethyl 17α-dichloroacetoxy-11β-hydroxyandrosta-1,4-dien-3-one-17β-carboxylate, having the structural formula

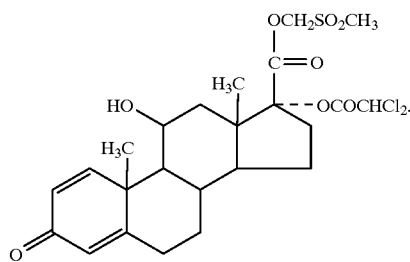

Repetition of the procedure described in the preceding paragraph, but using only 1 mmol of m-chloroperoxybenzoic acid, affords methylsulfinylmethyl 17α-dichloroacetoxy-11β-hydroxyandrosta-1,4-dien-3-one-17β-carboxylate.

EXAMPLE 16

Repetition of the procedure of the first paragraph of EXAMPLE 15, but substituting an equivalent quantity of one of the starting materials listed below for the 17α-dichloroacetoxy-11β-hydroxyandrosta-1,4-dien-3-one-17β-carboxylic acid there employed, affords the indicated products:

| STARTING MATERIAL | PRODUCT |
| --- | --- |
| 17α-dichloroacetoxy-9α-fluoro-11β-hydroxy-16α-methyl-androsta-1,4-dien-3-one-17β-carboxylic acid | methylthiomethyl 17α-dichloroacetoxy-9α-fluoro-11β-hydroxy-16α-methylandrosta-1,4-dien-3-one-17β-carboxylate |
| 16α,17α-bis(dichloroacetoxy)-9α-fluoro-11β-hydroxyandrosta-1,4-dien-3-one-17β-carboxylic acid | methylthiomethyl 16α,17α-bis(dichloroacetoxy)-9α-fluoro-11β-hydroxyandrosta-1,4-dien-3-one-17β-carboxylate |
| 17α-dichloroacetoxy-9α-fluoro-11β-hydroxyandrosta-1,4-dien-3-one-17β-carboxylic acid | methylthiomethyl 17α-dichloroacetoxy-9α-fluoro-11β-hydroxyandrosta-1,4-dien-3-one-17β-carboxylate |
| 17α-dichloroacetoxy-6α,9α-difluoro-11β-hydroxyandrosta-1,4-dien-3-one-17β-carboxylic acid | methylthiomethyl 17α-dichloroacetoxy-6α,9α-difluoro-11β-hydroxyandrosta-1,4-dien-3-one-17β-carboxylate |
| 9α,11β-dichloro-17α-dichloroacetoxyandrosta-1,4-dien-3-one-17β-carboxylic acid | methylthiomethyl 9α,11β-dichloro-17α-dichloroacetoxyandrosta-1,4-dien-3-one-17β-carboxylate |

EXAMPLE 17

Oxidation of each of the products obtained in EXAMPLE 16 in accordance with the procedure described in the second paragraph of EXAMPLE 15 affords, respectively:

methylsulfonylmethyl 17α-dichloroacetoxy-9α-fluoro-11β-hydroxy-16α-methylandrosta-1,4-dien-3-one-17β-carboxylate;

methylsulfonylmethyl 16α,17α-bis(dichloroacetoxy)-9α-fluoro-11β-hydroxyandrosta-1,4-dien-3-one-17β-carboxylate;

methylsulfonylmethyl 17α-dichloroacetoxy-9α-fluoro-11β-hydroxyandrosta-1,4-dien-3-one-17β-carboxylate;

methylsulfonylmethyl 17α-dichloroacetoxy-6α,9α-difluoro-11β-hydroxyandrosta-1,4-dien-3-one-17β-carboxylate; and methylsulfonylmethyl 9α,11β-dichloro-17α-dichloroacetoxyandrosta-1,4-dien-3-one-17β-carboxylate.

EXAMPLE 18

Oxidation of each of the products obtained in EXAMPLE 16 in accord with the procedure described in the third paragraph of EXAMPLE 15 affords, respectively:

methylsulfinylmethyl 17α-dichloroacetoxy-9α-fluoro-11β-hydroxy-16α-methylandrosta-1,4-dien-3-one-17β-carboxylate;

methylsulfinylmethyl 16α,17α-bis(dichloroacetoxy)-9α-fluoro-11β-hydroxyandrosta-1,4-dien-3-one-17β-carboxylate;

methylsulfinylmethyl 17α-dichloroacetoxy-9α-fluoro-11β-hydroxyandrosta-1,4-dien-3-one-17β-carboxylate;

methylsulfinylmethyl 17α-dichloroacetoxy-6α,9α-difluoro-11β-hydroxyandrosta-1,4-dien-3-one-17β-carboxylate; and methylsulfinylmethyl 9α,11β-dichloro-17α-dichloroacetoxyandrosta-1,4-dien-3-one-17β-carboxylate.

EXAMPLE 19

To a solution of 3 grams of chloromethyl 17α-dichloroacetoxy-11β-hydroxyandrosta-1,4-dien-3-one-17β-carboxylate in 100 mL of acetonitrile, a 10:1 molar ratio of AgF to steroid is added, and the mixture is stirred at room temperature for 12 days while shading the reaction systems from light. Thereafter, the reaction mixture is filtered, and the solid on the filter is thoroughly washed with ethyl acetate. The filtrate and the ethyl acetate solution are combined, and the mixture is washed with water and a saturated aqueous sodium chloride solution, and dried over anhydrous sodium sulfate. The solvents are distilled off, giving crude crystalline product. The product is subjected to preparative thin-layer chromatography (Silica Gel 60F254, Merck), using a mixture of chloroform and methanol (15:1) as an eluting solvent. Then the product is recrystallized from a mixture of tetrahydrofuran and n-hexane to give fluoromethyl 17α-dichloroacetoxy-11β-hydroxyandrosta-1,4-dien-3-one-17β-carboxylate.

EXAMPLE 20

Following the general procedure of EXAMPLE 19 and substituting therein the appropriate reactants affords the following compounds:

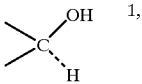

| Compound No. | $R_3$ | $R_4$ | $R_5$ | Z | Δ |
|---|---|---|---|---|---|
| 20-1 | α-CH₃ | F | H | >C(OH)(H) | 1, 4 |
| 20-2 | H | F | H | >C(OH)(H) | 1, 4 |
| 20-3 | H | F | F | >C(OH)(H) | 1, 4 |
| 20-4 | α-OCOCHCl₂ | F | H | >C(OH)(H) | 1, 4 |
| 20-5 | β-CH₃ | F | H | >C(OH)(H) | 1, 4 |
| 20-6 | H | F | α-CH₃ | >C(OH)(H) | 1, 4 |
| 20-7 | H | Cl | H | >C(OH)(H) | 1, 4 |

The foregoing compounds can be named as follows:
20-1: fluoromethyl 17α-dichloroacetoxy-9α-fluoro-11β-hydroxy-16α-methylandrosta-1,4-dien-3-one-17β-carboxylate
20-2: fluoromethyl 17α-dichloroacetoxy-9α-fluoro-11β-hydroxyandrosta-1,4-dien-3-one-17β-carboxylate
20-3: fluoromethyl 17α-dichloroacetoxy-6α,9α-difluoro-11β-hydroxyandrosta-1,4-dien-3-one-17β-carboxylate
20-4: fluoromethyl 16α,17α-bis(dichloroacetoxy)-9α-fluoro-11β-hydroxyandrosta-1,4-dien-3-one-17β-carboxylate
20-5: fluoromethyl 17α-dichloroacetoxy-9α-fluoro-11β-hydroxy-16β-methylandrosta-1,4-dien-3-one-17β-carboxylate
20-6: fluoromethyl 17α-dichloroacetoxy-9α-fluoro-11β-hydroxy-6α-methylandrosta-1,4-dien-3-one-17β-carboxylate
20-7: fluoromethyl 9α,11β-dichloro-17α-dichloroacetoxyandrosta-1,4-dien-3-one-17β-carboxylate

EXAMPLE 21

To a mixture of 9α-fluoro-11β,17α-dihydroxy-16α-methylandrosta-1,4-dien-3-one-17β-carboxylic acid (1 g, 2.64 mmol, 1 equivalent) and silver cyanide (0.78 g, 5.83 mmol, 2 equivalents) in 10 mL of HMPA (hexamethylphosphoramide, Aldrich), dichloroacetyl chloride (1.42 g, 9.63 nimol, 3.6 equivalents) was added in one portion at room temperature. The mixture was stirred in an oil bath at 80° C. for 12 minutes. Then, the mixture was added dropwise to saturated aqueous sodium chloride solution (200 mL) with stirring, forming a precipitate. The precipitate was collected by filtration and dissolved in tetrahydrofuran. The tetrahydrofuran solution was filtered to remove insoluble solid AgCN. The filtrate was concentrated to about 10 mL and precipitated by dilution with 200 mL of saturated aqueous NaCl solution. The collected precipitate (1.29 g, 100% yield) showed a single TLC spot with 13:100 MeOH/CH₂Cl₂. This precipitate could be directly used for next step without any purification. The colorless pure compound, 17α-dichloroacetoxy-9α-fluoro-11β-hydroxy-16α-methylandrosta-1,4-dien-3-one-17β-carboxylic acid, could be prepared for analysis by flash chromatography on silica gel with 13:100 MeOH/CH₂Cl₂, m.p. 217–218° C. ¹H NMR (CDCl₃-DMSO-d₆): 0.96 (3H, d, 16-CH₃), 1.12 (3H, s, 18-CH₃), 1.55 (3H, s, 19-CH₃), 2.59 (1H, m, 6α-H), 2.65 (1H, m, 6β-H), 3.42 (1H, m, 16β-H), 4.24 (1H, broad d, 11-H), 1.28, 1.76, 1.81, 1.84, 2.12, 2.16, 2.22 and 2.40 (8H, m, other H on ring), 6.03 (1H, s, 4-H), 6.25 (1H, d, 2-H), 6.43 (1H, s, CHCl₂), 7.33 (1H, d, 1-H) ppm.

EXAMPLE 22

To a mixture of 17α-dichloroacetoxy-9α-fluoro-11β-hydroxy-16α-methylandrosta-1,4-dien-3-one-17β-carboxylic acid (0.80 g, 1.63 mmol), sodium bicarbonate (0.69 g, 8.2 mmol, 5 equivalents) and tetrabutylammonium hydrogensulfate (0.11 g, 0.32 mmol, 0.2 equivalent) in 25 mL of water and 25 mL of methylene chloride was added iodoethane (0.54 g, 3.5 mmol, 2.1 equivalents) in 5 mL of methylene chloride at room temperature with vigorously stirring. The mixture was stirred at room temperature for 5 hours. The organic layer was separated and washed with saturated aqueous NaCl solution. Removal of solvent gave a crude product which was purified by flash chromatography on silica gel with 3.5:100 and 13:100 MeOH/methylene chloride to give ethyl 17α-dichloroacetoxy-9α-fluoro-11β-hydroxy-16α-methylandrosta-1,4-dien-3-one-17β-carboxylate (154 mg, 22.6%), m.p. 234–236° C. MS: 518.1 ([M+H]).

EXAMPLE 23

To a mixture of 11β,17α-dihydroxyandrosta-1,4-dien-3-one-17β-carboxylic acid (1.09 g, 3.14 mmol, 1 equivalent), NaHCO₃ (2.64 g, 31.4 mmol, 10 equivalents), tetrabutylammonium hydrogensulfate (0.31 g, 0.91 mmol, 0.3 equivalent) in methylene chloride and water (150 mL each) was added dichloroacetyl chloride (6.28 mmol, 2 equivalents) in 5 mL of methylene chloride at room temperature under vigorous stirring. The mixture was stirred at room temperature for 5 hours. The organic layer was separated and washed with saturated aqueous NaCl solution. Removal of solvent gave a crude product which was purified by flash chromatography on silica gel with 10:100 methanol/ methylene chloride to give pure 17α-dichloroacetoxy-11β-hydroxyandrosta-1,4-dien-3-one-17β-carboxylic acid in 95% yield.

Repetition of the foregoing procedure using chloroacetyl chloride in place of dichloroacetyl chloride afforded pure 17α-chloroacetoxy-11β-hydroxyandrosta-1,4-dien-3-one-17β-carboxylic acid in 84% yield.

Repetition of the procedure of the first paragraph of this example using α-chloropropionyl chloride in place of dichloroacetyl chloride afforded pure 17α-(α-chloro)propionyloxy-11β-hydroxyandrosta-1,4-dien-3-one-17β-carboxylic acid in 88% yield.

EXAMPLE 24

To a mixture of 17α-dichloroacetoxy-11β-hydroxyandrosta-1,4-dien-3-one-17β-carboxylic acid (3.24 g, 7.09 mmol, 1 equivalent), sodium bicarbonate (2.96 g, 35.4 mmol, 5 equivalents) and tetrabutylammonium hydrogensulfate (2.96 g, 8.72 mmol, 1.2 equivalents) in 60 mL of methylene chloride and 60 mL of water was added ethyl iodide (2.21 g, 14.17 mmol, 2 equivalents) in 5 mL of methylene chloride at room temperature under vigorous stirring. The mixture was stirred at room temperature for 5 hours. The organic layer was separated, washed with saturated aqueous NaCl solution, dried over sodium sulfate and rotoevaporated to give a crude product. The crude product was purified by flash chromatography on silica gel with 2.1:100 methanol/methylene chloride to give as a pure compound ethyl 17α-dichloroacetoxy- 11β-hydroxyandrosta-1,4-dien-3-one-17β-carboxylate (1.89 g, 54.9% yield), m.p. 207–208° C. MS: 484.8 ([M$^+$]).

Repetition of the general procedure described above, but using 17α-chloroacetoxy-11β-hydroxyandrosta-1,4-dien-3-one-17β-carboxylic acid as the steroidal starting material, afforded as a pure compound ethyl 17α-chloroacetoxy-11β-hydroxyandrosta-1,4-dien-3-one-17β-carboxylate in 31% yield, m.p. 169–171° C. MS: 450.2 ([M$^+$]).

In a similar manner, repetition of the general procedure described in the first paragraph of this example, but using 17α-(α-chloro)propionyloxy-11β-hydroxyandrosta-1,4-dien-3-one-17β-carboxylic acid as the steroidal starting material, afforded pure ethyl 17α-(α-chloro)propionyloxy-11β-hydroxyandrosta-1,4-dien-3-one-17β-carboxylate in 45.3% yield. MS: 465.4 ([M$^+$]).

EXAMPLE 25

To a mixture of unpurified 17α-dichloroacetoxy-9α-fluoro-11β-hydroxy-16α-methylandrosta-1,4-dien-3-one-17β-carboxylic acid (1 g, 2.0 mmol, 1 equivalent) prepared in EXAMPLE 21 and anhydrous K$_2$CO$_3$ (0.72 g, 5.21 mmol, 2.61 equivalents) in hexamethylphosphoramide (12 mL) was added methyl iodide (3.8 g, 26.8 mmol, 13.4 equivalents) at room temperature. The mixture was stirred at room temperature for 2 hours. The mixture was added to saturated aqueous NaCl solution (200 mL) under stirring, affording a precipitate. The precipitate was dissolved in methanol (200 mL). The methanol solution was precipitated by dilution with saturated aqueous NaCl solution (200 mL). The precipitate was purified by flash chromatography on silica gel (150 g) with 3:100 methanol/methylene chloride to give pure methyl 17α-dichloroacetoxy-9α-fluoro-11β-hydroxy-16α-methylandrosta-1,4-dien-3-one-17β-carboxylate (0.95 g, 92% yield calculated on the basis of the starting material of EXAMPLE 21, i.e. 9α-fluoro-11β,17α-dihydroxy-16α-methylandrosta-1,4-dien-3-one-17β-carboxylic acid). A sample for elemental analysis was obtained by dissolving the product in methylene chloride, filtering the solution and evaporating it to afford a solid, which was then crystallized from a mixture of methylene chloride and hexane, m.p. 252–253° C. $^1$H NMR (CDCl$_3$): 1.01 (3H, d, 16-CH$_3$), 1.09 (3H, s, 18-CH$_3$), 1.56 (3H, s, 19-CH$_3$), 2.43 (1H, m, 6α-H), 2.63 (1H, m, 6β-H), 3.38 (1H, m, 16β-H), 3.75 (3H, s, CO$_2$CH$_3$), 4.41 (1H, broad d, 11-H), 1.36, 1.64, 1.69, 1.72, 1.85, 2.18, 2.21 and 2.38 (8H, m, other H on ring), 5.94 ( 1H, s, CHCl$_2$), 6.13 (1H, s, 4-H), 6.35 (1H, d, 2-H), 7.22 (1H, d, 1-H) ppm.

When the above-described reaction was carried out using purified 17α-dichloroacetoxy-9α-fluoro-11β-hydroxy-16α-methylandrosta-1,4-dien-3-one-17β-carboxylic acid, the reaction yield was quantitative.

EXAMPLE 26

To a mixture of 17α-dichloroacetoxy-9α-fluoro-11β-hydroxy-16α-methylandrosta-1,4-dien-3-one-17β-carboxylic acid (.0.50 g, 1.02 mmol, 1 equivalent) and K$_2$CO$_3$ (0.36 g, 2.60 mmol, 2.6 equivalents) in hexamethylphosphoramide (10 mL) was added chloromethyl iodide (1.18 g, 6.69 mmol. 6.6 equivalents) at room temperature. The mixture was stirred at room temperature for 2 hours and then added to 200 mL of aqueous saturated NaCl solution. Air bubbles were blown through the aqueous solution to encourage formation of a precipitate. The precipitate was dissolved in methanol (10 mL) and added to saturated aqueous NaCl solution (200 mL). The precipitate which formed was purified by flash chromatography on silica gel (47 g) with 3:100 methanol/methylene chloride to give pure chloromethyl 17α-dichloroacetoxy-9α-fluoro-11β-hydroxy-16α-methylandrosta-1,4-dien-3-one-17β-carboxylate (0.29 g, 53% yield), melting at 228–229° C. (decomposition). $^1$H NMR (CDCl$_3$): 1.01 (3H, d, 16-CH$_3$), 1.16 (3H, s, 18-CH$_3$), 1.56 (3H, s, 19-CH$_3$), 2.42 (1H, m, 6α-H), 2.64 (1H, m, 6β-H), 3.42 (1H, m, 16β-H), 4.45 (1H, m, broad d, 11-H), 1.35, 1.63, 1.73, 1.78, 1.83, 1.88, 2.22 and 2.37 (8H, m, other H on ring), 5.56 and 5.94 (2H, 2d, CH$_2$Cl), 5.96 (1H, s, CHCl$_2$), 6.14 (1H, s, 6.37 (1H, d, 2-H), 7.23 (1H, d, 1-H)ppm. Analysis for C$_{24}$H$_{28}$ClFO$_6$: Cacld: C, 53.60; H, 5.25. Found: C, 53.81; H, 5.56.

EXAMPLE 27

| Ointment | |
|---|---|
| Compound of formula (I), e.g. ethyl or isopropyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.05% w/w |
| Liquid Paraffin | 10.0% w/w |
| White soft paraffin | 89.95% w/w |
| Aphthous Ulcer Pellet | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4- | 0.1 mg |

-continued

| | |
|---|---|
| dien-3-one-17β-carboxylate | |
| Lactose | 69.90 mg |
| Acacia | 3.00 mg |
| Magnesium stearate | 0.75 mg |
| Retention Enema | |
| | |
| Compound of formula (I), e.g. ethyl or isopropyl 17α-dichloroacetoxy-11β hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.001% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |
| Eye Drops | |
| | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.05% w/w |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

EXAMPLE 28

| | |
|---|---|
| Ointment | |
| | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.1% w/w |
| Liquid Paraffin | 10.0% w/w |
| White soft paraffin | 89.9% w/w |
| Aphthous Ulcer Pellet | |
| | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.15 mg |
| Lactose | 60.85 mg |
| Acacia | 3.00 mg |
| Magnesium stearate | 0.75 mg |
| Retention Enema | |
| | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.001% w/v |
| Tween 80 | 0.05% w/v |
| Ethanol | 0.015% w/v |
| Propylparaben | 0.02% w/v |
| Methylparaben | 0.08% w/v |
| Distilled water | q.s. 100 volumes |
| Eye Drops | |
| | |
| Compound of formula (I), e.g. | 0.1% w/v |

-continued

| | |
|---|---|
| isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | |
| Tween 80 | 2.5% w/v |
| Ethanol | 0.75% w/v |
| Benzalkonium chloride | 0.02% w/v |
| Phenyl ethanol | 0.25% w/v |
| Sodium chloride | 0.60% w/v |
| Water for injection | q.s. 100 volumes |

EXAMPLE 29

| | |
|---|---|
| Eye Drops | |
| | |
| Compound of formula (I), e.g. isopropyl or ethyl 17α-dichloroacetoxy-11β-hydroxyandrosta-1,4-dien-3-one-17β-carboxylate or methyl 17α-dichloroacetoxy-9α-fluoro-11β-hydroxy-16α-methylandrosta-1,4-dien-3-one-17β-carboxylate | 0.5% w/w |
| Povidone | 0.6% w/v |
| Benzalkonium chloride | 0.02% w/v |
| Sodium edetate U.S.P. | 0.10% w/v |
| Glycerin U.S.P. | 2.5% w/v |
| Tyloxapol U.S.P. | 3.0% w/v |
| Sodium chloride | 0.3% w/v |
| Sodium γ-aminobutyrate | 1.0% w/v |
| Sterile distilled water | q.s. 100 Volumes |

The ingredients listed above are combined, then the pH is checked and, if necessary, adjusted to 5.0–5.5 by basifying with sodium hydroxide or acidifying with hydrochloric acid.

In accord with one aspect of the invention, anti-inflammatory formulations like those of EXAMPLES 27–29 can be prepared by substituting a compound of formula (VI), e.g. ethyl 17α-(α-chloro)propionyloxy-11β-hydroxyandrosta-1,4-dien-3-one-17β-carboxylate, for the compound of formula (I) used in each formulation in EXAMPLES 27–29.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:
1. A compound having the formula

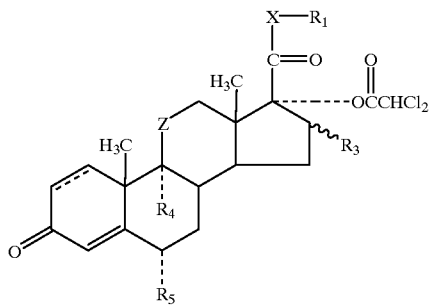

(I)

wherein:
$R_1$ is $C_1$–$C_4$ alkyl, which is unsubstituted or which bears one substituent selected from the group consisting of chloro, fluoro, $C_1$–$C_4$ alkoxy, $C_1$–$C_4$ alkylthio, $C_1$–$C_4$ alkylsulfinyl or $C_1$–$C_4$ alkylsulfonyl;
$R_3$ is hydrogen, α-hydroxy, β-hydroxy, α-methyl, β-methyl, =$CH_2$,

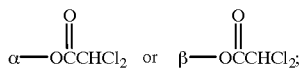

$R_4$ is hydrogen, fluoro or chloro;
$R_5$ is hydrogen, fluoro, chloro or methyl;
X is —O— or —S—;
Z is carbonyl, β-hydroxymethylene or β-chloromethylene;
and the dotted line in ring A indicates that the 1,2-linkage is saturated or unsaturated.

2. A compound as claimed in claim 1, wherein $R_3$ is hydrogen.
3. A compound as claimed in claim 1, wherein $R_3$ is α-methyl or β-methyl.
4. A compound as claimed in claim 1, wherein $R_3$ is α-hydroxy or β-hydroxy.
5. A compound as claimed in claim 1, wherein $R_3$ is α-OCOCHCl$_2$ or β-OCOCHCl$_2$.
6. A compound as claimed in claim 1, wherein $R_4$ is hydrogen.
7. A compound as claimed in claim 1, wherein $R_4$ is fluoro.
8. A compound as claimed in claim 1, wherein $R_5$ is hydrogen.
9. A compound as claimed in claim 1, wherein $R_5$ is fluoro.
10. A compound as claimed in claim 1, wherein $R_5$ is methyl.
11. A compound as claimed in claim 1, wherein $R_1$ is unsubstituted $C_1$–$C_4$ alkyl or chloromethyl.
12. A compound as claimed in claim 11, wherein $R_1$ is unsubstituted $C_1$–$C_4$ alkyl.
13. A compound as claimed in claim 12, wherein $R_1$ is methyl or ethyl.
14. A compound as claimed in claim 1, wherein X is —O—.
15. A compound as claimed in claim 1, wherein Z is β-hydroxymethylene.
16. A compound as claimed in claim 1, wherein the 1,2-linkage is unsaturated.

17. A compound as claimed in claim 1, having the formula

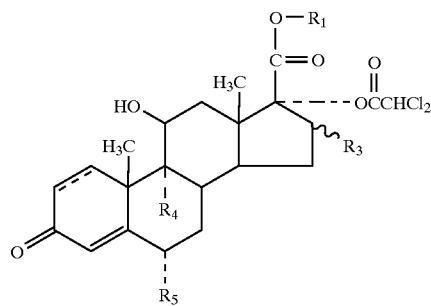

wherein $R_1$, $R_3$, $R_4$, $R_5$ and the dotted line are as defined in claim 1.
18. A compound as claimed in claim 17, wherein $R_3$ is hydrogen; $R_4$ is hydrogen or fluoro; and $R_5$ is hydrogen, fluoro or methyl.
19. A compound as claimed in claim 17, wherein $R_3$ is α-methyl or β-methyl; $R_4$ is hydrogen or fluoro; and $R_5$ is hydrogen, fluoro or methyl.
20. A compound as claimed in claim 17, wherein $R_3$ is α-hydroxy, β-hydroxy, α-OCOCHCl$_2$ or β-OCOCHCl$_2$; $R_4$ is hydrogen or fluoro; and $R_5$ is hydrogen, fluoro or methyl.
21. A compound as claimed in claim 17, wherein the 1,2-linkage is unsaturated.
22. A compound as claimed in claim 1, having the formula

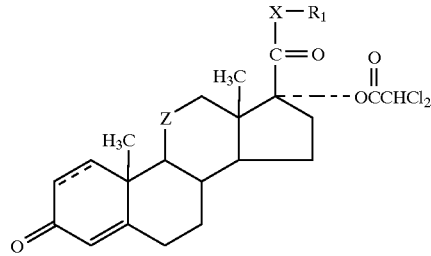

wherein $R_1$, X and Z are as defined in claim 1.
23. A compound as claimed in claim 22, wherein $R_1$ is unsubstituted $C_1$–$C_4$ alkyl or chloromethyl.
24. A compound as claimed in claim 23, wherein Z is β-hydroxymethylene.
25. A compound as claimed in claim 1, having the formula

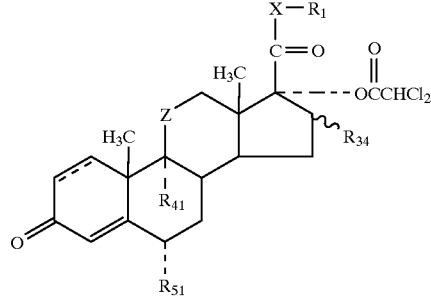

wherein $R_1$, X and Z are as defined in claim 1; $R_{34}$ is hydrogen or α-hydroxy; $R_{41}$ is hydrogen or fluoro; $R_{51}$ is hydrogen or fluoro; and the dotted line in ring A indicates that the 1,2-linkage is saturated or unsaturated.
26. A compound as claimed in claim 25, wherein $R_1$ is unsubstituted $C_1$–$C_4$ alkyl or chloromethyl.

27. A compound as claimed in claim 26, wherein Z is β-hydroxymethylene.

28. A compound as claimed in claim 1, having the formula

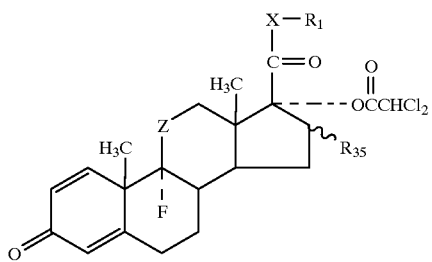

wherein $R_1$, X and Z are as defined in claim 1 and $R_{35}$ is α-OCOCHCl$_2$ or β-OCOCHCl$_2$.

29. A compound as claimed in claim 28, wherein $R_1$ is unsubstituted $C_1$–$C_4$ alkyl or chloromethyl.

30. A compound as claimed in claim 29, wherein Z is β-hydroxymethylene.

31. A compound as claimed in claim 1, having the formula

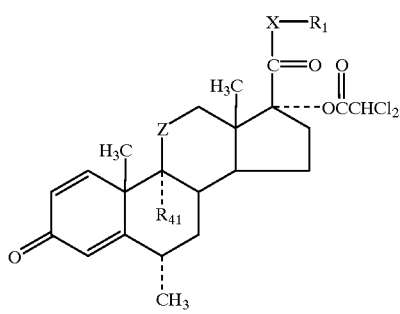

wherein $R_1$, X and Z are as defined in claim 1 and $R_{41}$ is hydrogen or fluoro.

32. A compound as claimed in claim 31, wherein $R_1$ is unsubstituted $C_1$–$C_4$ alkyl or chloromethyl.

33. A compound as claimed in claim 32, wherein Z is β-hydroxymethylene.

34. A compound as claimed in claim 1, having the formula

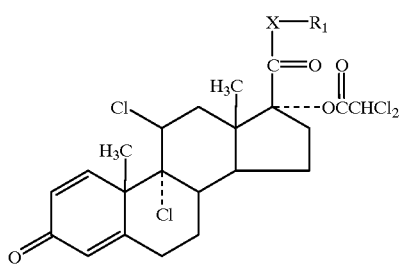

wherein X and $R_1$ are as defined in claim 1.

35. A compound as claimed in claim 34, wherein $R_1$ is unsubstituted $C_1$–$C_4$ alkyl or chloromethyl.

36. A compound as claimed in claim 1, having the formula

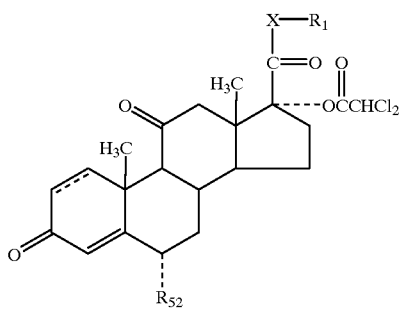

wherein X and $R_1$ are as defined in claim 1, $R_{52}$ is hydrogen or chloro and the dotted line in ring A indicates that the 1,2-linkage is saturated or unsaturated.

37. A compound as claimed in claim 36, wherein $R_1$ is unsubstituted $C_1$–$C_4$ alkyl or chloromethyl.

38. A compound as claimed in claim 1, having the formula (Ia)

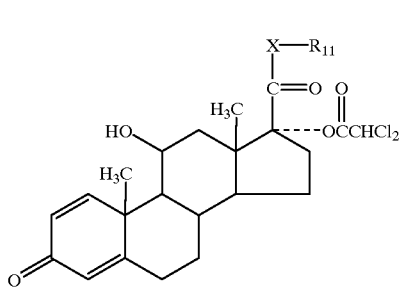

wherein $R_{11}$ is unsubstituted $C_1$–$C_4$ alkyl or chloromethyl.

39. The compound as claimed in claim 38, which is methyl 17α-dichloroacetoxy-11β-hydroxyandrosta-1,4-dien-3-one-17β-carboxylate.

40. The compound as claimed in claim 38, which is ethyl 17α-dichloroacetoxy-11β-hydroxyandrosta-1,4-dien-3-one-17β-carboxylate.

41. The compound as claimed in claim 38, which is isopropyl 17α-dichloroacetoxy-11β-hydroxyandrosta-1,4-dien-3-one-17β-carboxylate.

42. The compound as claimed in claim 38, which is chloromethyl 17α-dichloroacetoxy-11β-hydroxyandrosta-1,4-dien-3-one-17β-carboxylate.

43. A compound as claimed in claim 1, having the formula (Ib)

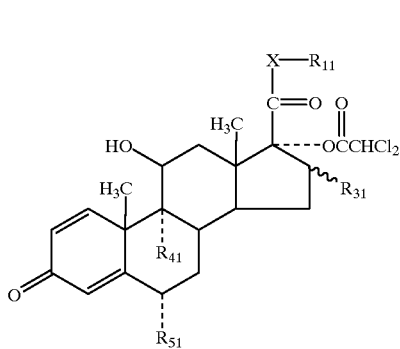

wherein $R_{11}$ is unsubstituted $C_1$–$C_4$ alkyl or chloromethyl; $R_{41}$ is hydrogen or fluoro; and $R_{51}$ is hydrogen or fluoro.

44. The compound as claimed in claim 43, which is methyl 17α-dichloroacetoxy-9α-fluoro-11β-hydroxy-16α-methylandrosta-1,4-dien-3-one-17β-carboxylate.

45. The compound as claimed in claim 43, which is ethyl 17α-dichloroacetoxy-9α-fluoro-11β-hydroxy-16α-methylandrosta-1,4-dien-3-one-17β-carboxylate.

46. The compound as claimed in claim 43, which is chloromethyl 17α-dichloroacetoxy-9α-fluoro-11β-hydroxy-16α-methylandrosta-1,4-dien-3-one-17β-carboxylate.

47. A compound having the formula

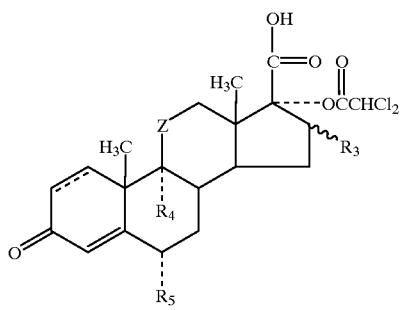

wherein:

$R_3$ is hydrogen, α-hydroxy, β-hydroxy, α-methyl, β-methyl, =CH$_2$,

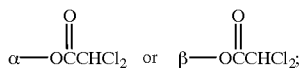

$R_4$ is hydrogen, fluoro or chloro;

$R_5$ is hydrogen, fluoro, chloro or methyl;

Z is carbonyl, β-hydroxymethylene or β-chloromethylene;

and the dotted line in ring A indicates that the 1,2-linkage is saturated or unsaturated.

48. A compound according to claim 47, wherein Z is β-hydroxymethylene.

49. A compound according to claim 48, wherein $R_4$ is hydrogen or fluoro and $R_5$ is hydrogen, fluoro or methyl.

50. A compound according to claim 47, having the formula

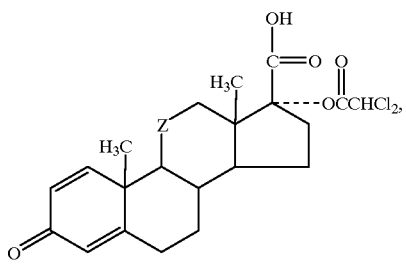

wherein Z is as defined in claim 47.

51. A compound according to claim 47, having the formula

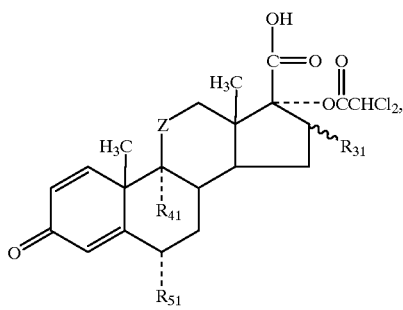

wherein Z is as defined in claim 47; $R_{31}$ is α-CH$_3$ or β-CH$_3$; $R_{41}$ is hydrogen or fluoro; and $R_{51}$ is hydrogen or fluoro.

52. A compound according to claim 47, having the formula

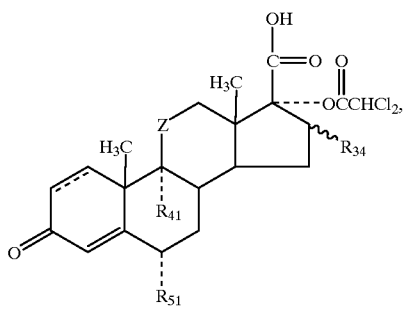

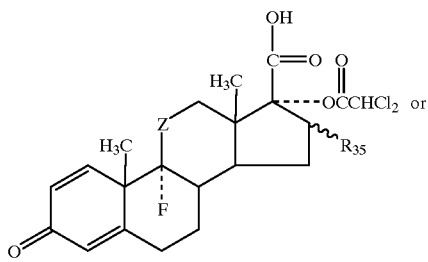

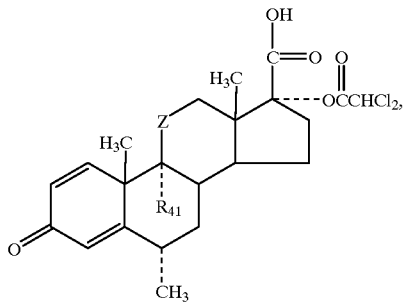

wherein Z and the dotted line are as defined in claim 47; $R_{34}$ is hydrogen or α-hydroxy; $R_{41}$ is hydrogen or fluoro; $R_{51}$ is hydrogen or fluoro; and $R_{35}$ is α-OCOCHCl$_2$ or β-OCOCHCl$_2$.

53. The compound according to claim 50, which is 17α-dichloroacetoxy-11β-hydroxyandrosta-1,4-dien-3-one-17β-carboxylic acid.

54. A compound according to claim 51, wherein Z is β-hydroxymethylene.

55. The compound according to claim 51, which is 17α-dichloroacetoxy-9α-fluoro-11β-hydroxy-16α-methylandrosta-1,4-dien-3-one-17β-carboxylic acid.

56. A compound according to claim 52, wherein Z is β-hydroxymethylene.

57. A pharmaceutical composition comprising an anti-inflammatory effective amount of a compound as claimed in claim 1 and a non-toxic pharmaceutically acceptable carrier therefor suitable for topical or other local application.

58. An ophthalmic composition comprising an anti-inflammatory effective amount of a compound as claimed in claim 1 and a non-toxic ophthalmically acceptable carrier therefor.

59. A method for alleviating inflammation in or on a warm-blooded animal exhibiting a localized inflammatory response, which comprises locally administering to said animal an anti-inflammatory effective amount of a compound as claimed in claim 1.

60. A method for alleviating inflammation in or on a warm-blooded animal exhibiting a topical inflammatory response, which comprises topically administering to said animal an anti-inflammatory effective amount of a compound as claimed in claim 1.

61. A method for alleviating inflammation in the eye or eyes of a warm-blooded animal exhibiting an ophthalmic inflammatory response, which comprises administering to the eye or eyes of said animal an anti-inflammatory effective amount of a compound as claimed in claim 1.

62. A method for alleviating inflammation of the nasal mucosa in a warm-blooded animal exhibiting a nasal inflammatory response, which comprises nasally administering to said animal an anti-inflammatory effective amount of a compound as claimed in claim 1.

63. A method for alleviating asthma in a warm-blooded animal exhibiting an asthmatic inflammatory response, which comprises administering to said animal by oral inhalation an anti-inflammatory effective amount of a compound as claimed in claim 1.

64. A method for alleviating inflammation of the upper or lower intestine in a warm-blooded animal exhibiting an intestinal inflammatory response, which comprises rectally administering to said animal an anti-inflammatory effective amount of a compound as claimed in claim 1.

65. A method for alleviating inflammation of the upper or lower intestine in a warm-blooded animal exhibiting an intestinal inflammatory response, which comprises orally administering to said animal an anti-inflammatory effective amount of a compound as claimed in claim 1.

66. A method for alleviating inflammation in the ear or ears of a warm-blooded animal exhibiting an otic inflammatory response, which comprises administering to the ear or ears of said animal an anti-inflammatory effective amount of a compound as claimed in claim 1.

67. A method for alleviating inflammation in a joint or joints of a warm-blooded animal exhibiting an arthritic inflammatory response, which comprises injecting into said joint or joints an anti-inflammatory effective amount of a compound as claimed in claim 1.

68. A method for alleviating inflammation of the skin of a warm-blooded animal exhibiting a dermal inflammatory response, which comprises dermally administering to said animal an anti-inflammatory effective amount of a compound as claimed in claim 1.

69. A method for alleviating inflammation of the mouth, gums or throat of a warm-blooded animal exhibiting an oral, gingival or throat inflammatory response, which comprises orally administering to said animal an anti-inflammatory effective amount of a compound as claimed in claim 1.

* * * * *